(12) United States Patent
Thiel et al.

(10) Patent No.: US 6,773,916 B1
(45) Date of Patent: Aug. 10, 2004

(54) AGENTS AND METHODS FOR TREATMENT AND DIAGNOSIS OF OCULAR DISORDERS

(75) Inventors: Michael Alexander Thiel, Zurich (CH); Heddy Zola, Evandale (AU); Douglas John Coster, Heathpool (AU); Keryn Anne Williams, Kingswood (AU)

(73) Assignee: The Flinders University of South Australia (AU)

( * ) Notice: Subject to any disclaimer, the term of this patent is extended or adjusted under 35 U.S.C. 154(b) by 0 days.

(21) Appl. No.: 09/857,399

(22) PCT Filed: Dec. 24, 1999

(86) PCT No.: PCT/AU99/01163

§ 371 (c)(1),
(2), (4) Date: Sep. 19, 2001

(87) PCT Pub. No.: WO00/40262

PCT Pub. Date: Jul. 13, 2000

(30) Foreign Application Priority Data

Jan. 5, 1999 (AU) ............................................... PP8033
Oct. 7, 1999 (AU) ............................................... PQ3305

(51) Int. Cl.$^7$ ............................ C12N 5/16; C07K 16/00
(52) U.S. Cl. .................... 435/326; 435/334; 530/388.3; 530/388.5
(58) Field of Search ............................... 435/326, 334; 530/388.3, 388.5

(56) References Cited

U.S. PATENT DOCUMENTS 5,616,122 A 4/1997 Lam et al.
5,670,626 A 9/1997 Chang ..................... 530/388.5

FOREIGN PATENT DOCUMENTS

| WO | WO 93/06865 | 4/1993 |
| WO | WO 94/09817 | 5/1994 |
| WO | WO 94/14475 | 7/1994 |
| WO | WO 97/43416 A1 | 11/1997 |
| WO | WO 99/58570 | 11/1999 |

OTHER PUBLICATIONS

K. Morimoto et al., *Effect of Medium–Chain Fatty Acid Salts on Penetration of a Hydrophilic Compound and a Macromolecular Compound across Rabbit Corneas*, Arch. Int. Pharmacodyn, vol. 302, 1989, pp. 18–26.

Wen–Pin Yang et al., *Design and Evaluation of a Thrombin–Activable Plasminogen Activator*, Biochemistry, vol. 33, 1994, pp. 2306–2312.

*Detection of Cytokine Receptors by Flow Cytometry*, John Wiley & Sons, Inc., vol. 6, No. 21.1, 1995, pp. 1–18.

E. Sally Ward et al., *Binding activities of a repertoire of single immunoglobulin variable domains secreted from Escherichia coli*, Nature, vol. 341, Oct. 12, 1989, pp. 544–546.

R.M. Broekhuyse et al., *Opsin–induced experimental autoimmune retinitis in rats*, Current Eye Research, vol. 3, No. 12, 1984, pp. 1405–1412.

N.L. Burstein, Preservative cytotoxic threshold for benzalkonium chloride and chlorhexidine digluconate in cat and rabbit corneas, *Invest. Ophthalmol. Vis. Sci.*, Mar. 1980, pp. 308–313.

(List continued on next page.)

*Primary Examiner*—Hankyel T. Park
(74) *Attorney, Agent, or Firm*—Beth A. Burrous; Foley & Lardner LLP

(57) ABSTRACT

A method of treating an ocular disorder is disclosed, comprising administering to a patient in need of such treatment, an effective amount of a sub-immunoglobulin antigen-binding molecule that is immuno-interactive with a target antigen associated with the disorder. The invention is also directed to compositions comprising this sub-immunoglobulin antigen-binding molecule and to a method of diagnosing an ocular condition using such molecule.

64 Claims, 14 Drawing Sheets

OTHER PUBLICATIONS

Tang–Liu et al., *Effects of Four Penetration Enhancers on Corneal Permeability of Drugs in Vitro*, Journal of Pharmaceutical Sciences, vol. 83, No. 1, Jan. 1994, pp. 85–90.

P. Ashton et al., *Location of Penetration of Metabolic Barriers to Levobunolol in the Corneal Epithelium of the Pigmented Rabbit*, The Journal of Pharmacology and Experimental Therapeutics, vol. 259, No. 2, 1991, pp. 719–724.

N.L. Burstein, *The Effects of Topical Drugs and Preservatives on the Tears and Corneal Epithelium in Dry Eye*, Trans. Ophthalmol. Soc. U.K., vol. 104, 1985, pp. 402–409.

J.D. Söderholm, M.D. et al., *Reversible Increase in Tight Junction Permeability to Macromolecules in Rat Ileal Mucosa In Vitro by Sodium Caprate, a Constituent of Milk Fat*, Digestive Diseases and Sciences, vol. 43, No. 7, Jul. 1998, pp. 1547–1552.

Shu–Wen Chang et al., *The Epithelial Barrier Function in Clear Corneal Grafts*, Ophthalmic Res, vol. 26, 1994, pp. 283–289.

H.F. Edelhauser et al., *Corneal Epithelial Tight Junctions and the Localization of Surface Mucin*, Lacrimal Gland, Tear Film, and Dry Eye Syndromes 2, 1998, pp. 265–271.

N.L. Burstein et al., *Review: Corneal Penetration and Ocular Bioavailability of Drugs*, Journal of Ocular Pharmacology, vol. 1, No. 3, 1985, pp. 309–326.

D.M. Maurice, *Structures and Fluids Involved in the Penetration of Topically Applied Drugs*, pp. 7–20.

R. Osusky et al., *Diffusion of immunoglobulins into rabbit cornea after subconjunctival injection: experimental demonstration and mathematical model*, Graef's Arch Clin Exp Ophthalmol, vol. 231, 1993, pp. 122–128.

M. Araie, *Kinetics of Intraocular Penetration of Topical Fluorescein: Analysis by New Method*, J. Ophthalmol, vol. 27, 1983, pp. 421–433.

J.S. Huston et al., *Single–chain Fv radioimmunotargeting*, The Quarterly Journal of Nuclear Medicine, vol. 10, 1996, pp. 320–333.

Massimo Fresta, *Characterization and In–Vivo Ocular Absorption of Liposome–encapsulated Acyclovir*, J. Pharm. Pharmacol. vol. 51, 1999, pp. 565–576.

J. Frucht–Pery et al., *Efficacy of iontophoresis in the rat cornea*, Graef's Arch Clin Exp Ophthalmol, vol. 234, 1996, pp. 765–769.

I.G. Barr et al., *ISCOMs and other saponin based adjuvants*, Advanced Drug Delivery Reviews, vol. 32, 1998, pp. 247–271.

J. Davies et al., *'Camelising' human antibody fragments: NMR studies on VH domains*, FEBS Letters, vol. 339, 1994, 285–290.

K.O. Webber et al., *Preparation and Characterization of A Disulfide–Stabilized Fv Fragment of the Anti–Tac Antibody: Comparison with its Single–Chain Analog*, Molecular Immunology, vol. 32, No. 4, 1995, pp. 249–258.

D.M. Maurice et al., *Diffusion Across the Sclera*, Exp. Eye Res., vol. 25, 1977, pp. 577–582.

C.A. Adler et al., *The Effect of Viscosity of the Vehicle on the Penetration of Fluorescein into the Human Eye*, Exptl Eye Res. vol. 11, 1971, pp. 34–42.

M. Göbbels et al., *Impairment of corneal epithelial barrier function in diabetics*, Graefe's Archive Ophthalmology, vol. 227, 1989, pp. 142–144.

H. Sasaki et al., *Different Effects of Absorption Promoters on Corneal and Conjunctival Penetration of Ophthalmic Beta–Blockers*, Pharmaceutical Research, vol. 12, No. 8, 1995, pp. 1146–1150.

John E. Oakes, et al., *Role of Fc Fragments in Antibody–Mediated Recovery from Ocular and Subcutaneous Herpes Simplex Virus Infections*, Infection and Immunity, vol. 33, No. 1, Jul. 1981, pp. 109–114.

Manfred Birchler et al., *Selective targeting and photocoagulation of ocular angiogenesis mediated by a phage–derived human antibody fragment*, Nature Biotechnology, vol. 17, Oct. 1999, pp. 984–988.

Gregory P. Adams et al., *Highly Specific in Vivo Tumor Targeting by Monovalent and Divalent Forms of 741F8 Anti–c–erB–2 Single–Chain Fv$^1$*, Cancer Research, vol. 53, Sep. 1, 1993, pp. 4026–4034.

W. Ayliffe et al., *Prolongation of rat corneal graft survival by treatment with anti–CD4 monoclonal antibody*, British Journal of Ophthalmology, vol. 76, 1992, pp. 602–606.

Paul R. Badenoch, BSc (Hons) et al., *Pathogenicity of Acanthamoeba and a Corynbacterium in the Rat Cornea*, Arch Ophthalmol, vol. 108, Jan. 1990, pp. 107–112.

Badenoch et al., *Corneal Virulence, Cytopathic Effect on Human Keratocytes and Genetic Characaterization of Acanthamoeba*, Intn'l. Journal of Parasitology, vol. 25, 1995, pp. 229–239.

Behar–Cohen et al., *Reduction of Corneal Edema in Endotoxin–Induced Uveitis after Application of L–Name as Nitric Oxide Synthase Inhibitor in Rats by Iontophoresis*, Investigative Ophthalmology & Visual Science, vol. 39, No. 6, May 1998, pp. 897–904.

K. Bosslet et al., *Molecular and functional characterisation of a fusion protein suited for tumour specific prodrug activation*, Br. J. Cancer, vol. 65, 1992, pp. 234–238.

Bothmann et al., *Selection for a periplasmic factor improving phage display and functional periplasmic expression*, Nature Biotechnology, vol. 16, Apr. 1998, pp. 376–380.

Broekhuyse et al., *Experimental Melanin–Protein Induced Uveitis (EMIU) is the Sole Type of Uvetis Evoked by a Diversity of Ocular Melanin Preparations and Melanin–Derived Soluble Polypeptides*, Jpn. J. Ophthalmol, vol. 40, 1996, pp. 459–468.

Broekhuyse et al., *Multiple recurrences in melanin–protein–induced uveitis in the rat*, Ocular Immunology and Inflammation, vol. 3, No. 3, 1995, pp. 149–155.

Brooks et al., *Acanthamoeba Keratitis*, Cornea, vol. 13, No. 2, 1994, pp. 186–189.

Chang, M.D., et al., *Changes in Corneal Autofluorescence and Corneal Epithelial Barrier Function With Agin*, Cornea, vol. 12, No. 6, 1993, pp. 493–499.

Chapman et al., *Therapeutic antibody fragments with prolonged in vivo half–lives*, Nature Biotechnology, vol. 17, Aug. 1999. pp. 780–783.

Cumber et al., *Comparative Stabilities In Vitro and In Vivo of a Recombinant Mouse Antibody FvCys Fragment and a bisFvCys Conjugate*, The Journal of Immunology, vol. 149, No. 1, Jul. 1, 1992, pp. 120–126.

George et al., *Radiometal labeling of recombinant proteins by a genetically engineered minimal chelation site: Technetium–99m coordination by single–chain Fv antibody fusion proteins through a C–terminal cysteinyl peptide*, Proc. Natl. Acad. Sci USA, vol. 92, Aug. 1995, pp. 8358–8362.

Glockshuber et al., *A Comparison of Strategies To Stabilize Immunoglobulin $F_v$–Fragments*, Biochemistry, vol. 29, 1990, pp. 1362–1367.

Goshorn et al., *Genetic Construction, Expression, and Characterization of a Single Chain Anti–Carcinoma Antibody Fused to β–Lactamase*, Cancer Research, vol. 53, May 1, 1993, pp. 2123–2127.

Green et al., *Influence of Various Agents on Corneal Permeability*, American Journal of Ophthalmology, vol. 27, No. 5, Nov. 1971, pp. 897–905.

Hamers–Casterman et al, *Naturally occurring antibodies devoid of light chains*, Nature, vol. 363, Jun. 3, 1993, pp. 446–448.

He et al., *Promotion of Murine Orthotopic Corneal Allograft Survival by Systemic Administration of Anti–CD4 Monoclonal Antibody*, Investigative Ophthalmology & Visual Science, vol. 32, No. 10, Sep. 1991, pp. 2723–2728.

Hendricks Ph.D., *An Immunologist's View of Herpes Simplex Keratitis: Thygeson Lecture 1996, Presented at the Ocular Microbiology and Immunology Group Meeting*, Oct. 26, 1996, Cornea, vol. 16, No. 5, 1997, pp. 503–506.

The Herpetic Eye Disease Study Group, *Acyclovir for the Prevention of Recurrent Herpes Simplex Virus Eye Disease*, The New England Journal of Medicine, vol. 339, No. 5, Jul. 30, 1998, pp. 300–306.

Holvoet et al., *Characterization of a Chimeric Plasminogen Activator Consisting of a Single–chain Fv Fragment Derived from a Fibrin Fragment D–Dimer–specific Antibody and a Truncated Single–chain Urokinase*, The Journal of Biological Chemistry, vol. 266, No. 29, Oct. 15, 1991, pp. 19717–19724.

Kostelny et al., *Formation of a Bispecific Antibody by the Use of Leucine Zippers*, The Journal of Immunology, vol. 148, No. 5, Mar. 1, 1992, pp. 1547–1553.

Krebber et al., *Reliable cloning of functional antibody variable domains from hybridomas and spleen cell repertoires employing a reengineered phage display system*, Journal of Immunological Methods, vol. 201, 1997, pp. 35–55.

Ku et al., *Alternate protein frameworks for molecular recognition*, Proc. Natl. Acad. Sci. USA, vol. 92, Jul. 1995, pp. 6552–6556.

Laycock et al., *Characterization of a Murine Model of Recurrent Herpes Simplex Viral Keratitis Induced by Ultraviolet B Radiation*, Investigative Ophthalmology & Visual Science, vol. 32, No. 10, Sep. 1991, pp. 2741–2746.

Masuda et al., *Gene Transfer With Liposomes to the Intraocular Tissues by Different Routes of Administration*, Investigative Ophthalmology & Visual Science, vol. 37, No. 9, Aug. 1996, pp. 1914–1920.

Mishima, S., *Clinical pharmacokinetics of the eye*, Investigative Ophthalmology Visual Science, vol. 21, pp. 504–541.

Olsen et al., *Human Scleral Permeability Effects of Age, Cryotherapy, Transscleral Diode Laser, and Surgical Thinning*, Investigative Ophthalmology & Visual Science, vol. 36, No. 9, Aug. 1995, pp. 1893–1903.

Pack et al., *Miniantibodies: Use of Amphipathic Helices To Produce Functional, Flexibly Linked Dimeric Fv Fragments with High Avidity in Escherichia coli*, Biochemistry, vol. 31, No. 6, Feb. 18, 1992, pp. 1579–1584.

Pleyer et al., *Effect of Topically Applied Anti–CD4 Monoclonal Antibodies on Orthotopic Corneal Allografts in a Rat Model*, Investigative Ophthalmology & Visual Science, vol. 36, No. 1, Jan. 1995, pp. 52–61.

Pluckthun et al., *Producing antibodies in Escherichia coli: from PCR to fementation*, Chapter 10, pp. 203–252.

Reiter et al., *Improved Binding and Antitumor Activity of a Recombinant Anti–erbB2 Immunotoxin by Disulfide Stabilzation of the Fv Fragment*, The Journal of Biological Chemistry, vol. 269, No. 28, Jul. 15, 1994, pp. 18327–18331.

Reiter et al., *Stabilization of the Fv Fragments in Recombinant Immunotoxins by Disulfide Bonds Engineered into Conserved Framework Regions*, Biochemistry, vol. 33, 1994, pp. 5451–5459.

Reiter et al., *Antitumor Activity and Pharmacokinetics in Mice of a Recombinant Immunotoxin Containing a Disulfide–stabilized Fv Fragment*, Cancer Research, vol. 54, May 15, 1994, pp. 2714–2718.

Rodriques et al., *Development of a Humanized Disulfide–stabilized Anti–p185$^{HER2}$ Fv–β–Lactamase Fusion Protein for Activation of a Cephalosporin Doxorubicin Prodrug*, Cancer Research, vol. 55, Jan. 1, 1995, pp. 63–70.

Rosenbaum et al., *Endotoxin–induced uveitis in rats as a model for human disease*, Nature, vol. 286, Aug. 7, 1980, pp. 611–613.

Rothhava, M.D., et al., *Clinical Features of Acute Anterior Uveitis*, American Journal of Ophthalmology, vol. 103, Feb. 1987, pp. 137–145.

Schwarze et al., *In Vivo Protein Transduction: Delivery of a Biologically Active Protein into the Mouse*, Science, vol. 285, Sep. 3, 1999, pp. 1569–1572.

Shimazaki, M.D., et al., *Morphology and Barrier Function of the Corneal Epithelium After Peneftrating Keratoplasty: Association with Original Diseases, Tear Function, and Suture Removal*, Cornea, vol. 18, No. 5, 1999, pp. 559–564.

Smith et al., *Mice Deficient in Tumor Necrosis Factor Receptors p55 and p75, Interleukin–4, or Inducible Nitric Oxide Synthase AreSusceptible to Endotoxin–Induced Uveitis*, IOVS, vol. 39, No. 3, Mar. 1998, pp. 658–661.

Smith et al., *Basic pathogenic mechanisms operating in experimental models of acute anterior uveitis*, Immunology and Cell Biology, vol. 76, 1998, pp. 497–512.

Smith et al., *Experimental melanin–induced uveitis in the Fischer 344 rat is inhibited by anti–Cd4 monoclonal antibody, but not by mannose–6–phosphate*, Clin Exp Immunol, vol. 115, 1999, pp. 64–71.

Streilein et al., *Immunity causing blindness: five different paths to herpes stromal keratitis*, Immunology Today, vol. 18, No. 9, Sep. 1997, pp. 443–449.

Tanihara et al., *Prolonged Impairment of Peripheral Corneal Epithelium Barrier Function After Successful Trabeculectomy*, American Journal of Ophthalmology, vol. 123, No. 4, 1997, pp. 487–493.

Thiel et al., *A simple corneal perfusion chamber for drug penetration and toxicity studies*, British Journal of Ophthalmology, vol. 85, Sep. 13, 2000, pp. 450–453.

Thiel et al., *Antibody engineering, The Basics*, 2000, pp. 45–66.

Thomas et al., *Immunopathology of Herpetic Stromal Keratitis: Discordance in CD4+ T Cell Function Between Eughymic Host and Reconstituted SCID Recipients*, The Journal of Immunology, pp. 3965–3970.

Verhagen et al., *Diffusion of Immunoglobulin G from the Vascular Compartment into the Normal Rabbit Cornea*, Investigative Ophthalmology & Visual Science, vol. 31, No. 8, Aug. 1990, pp. 1519–1525.

Williams et al., *Corneal Transplantation in Small Animals, Experimental Transplantation Models in Small Animals*, eds., MK Green, TE Mandel, Chur, Switzerland: Harwood Academic Publishers, vol. 5, 1995, pp. 107–132.

Williams et al., *Penetrating Corneal Transplantation in the Inbred Rat: A New Model, Investigative Ophthalmology & Visual Science*, vol. 26, Jan. 1985, pp. 23–30.

Williams et al., *The Australian Corneal Graft Registry*, 1990–1992 Report, pp. 48.

Williams et al., *Patterns of Corneal Graft Rejection in the Rabbit and Reversal of Rejection With Monoclonal Antibodies,Transplantation*, vol. 54, No. 1, Jul. 1992, pp. 38–43.

Williams et al., *Clinical and Experimental Aspects of Corneal Transplantation, Transplantation Reviews*, vol. 7, No. 1, Jan. 1993, pp. 44–64.

Winter et al., *Man–made antibodies, Nature*, vol. 349, Jan. 24, 1991, pp. 293–299.

Yokoi et al., *Impairment of ocular surface epithelium barrier function in patients with atopic dermatitis, British Journal of Ophthalmology*, vol. 82, 1998, pp. 797–800.

Zola et al., *Detection by immunofluorescence of surface molecules present in low copy numbers, Journal of Immunological Mehtods*, vol. 135, 1990, pp. 247–255.

Sergieva et al., "Radioimmunoscintigraphy in Patients with Ocular Melanoma," *Clinical Nuclear Medicine*, Jan. 1997, pp. 25–29, vol. 22, No. 1, © Lippincott–Raven Publishers.

Scheidler et al., "Immunoimaging of choroidal melanoma: assessment of its diagnostic accuracy and limitations in 101 cases," *British Journal of Ophthalmology*, 1992, pp. 457–460, vol. 76, No. 8.

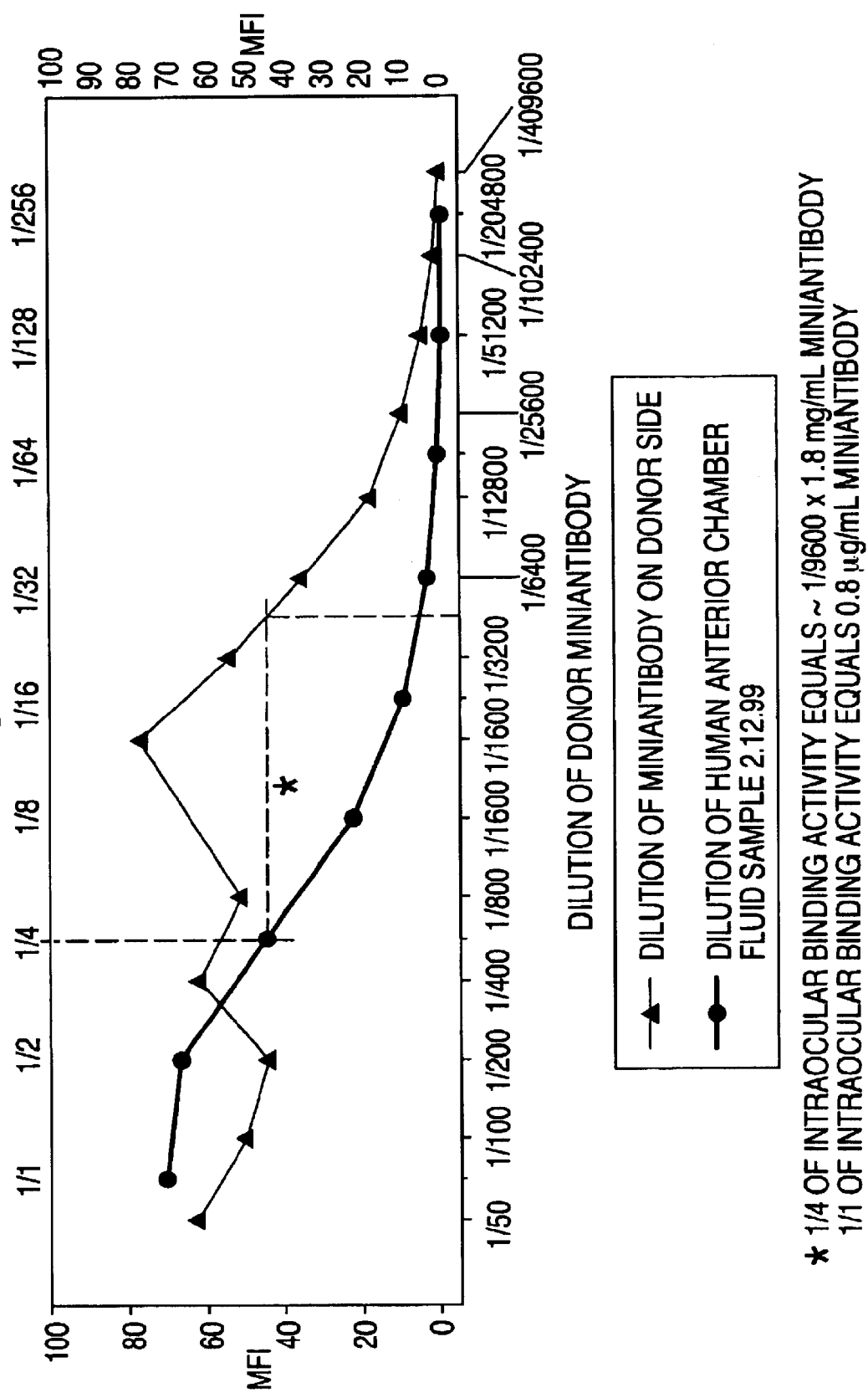

AGENTS AND METHODS FOR TREATMENT AND DIAGNOSIS OF OCULAR DISORDERS

This is the National Phase of International Application PCT/AU99/01163, filed Dec. 24, 1999, which claims priority of Australian Applications PP8033, filed Jan. 5, 1999 and PQ 3305, filed Oct. 7, 1999, both of which are herein incorporated by reference.

FIELD OF THE INVENTION

The present invention relates, in general, to treatment and diagnosis of ocular disorders. More particularly, the invention is concerned with methods of treating and diagnosing ocular disorders using sub-immunoglobulin antigen-binding molecules.

BACKGROUND OF THE INVENTION

Various ocular disorders are known but for many of these, there are less than optimal methods of treatment or diagnosis available. For example, acute anterior uveitis, an inflammation of the iris and ciliary body, is a common condition with a lifetime cumulative incidence of 0.4% in the general population (Rothova et al, 1987, *Am. J. Opthalmol.* 103: 137–145). Disease tends to start in childhood or young adulthood, is frequently bilateral and is generally recurrent. Acute anterior uveitis is painful, is almost always associated with some morbidity, and can be blinding. This disease is an antigen driven, delayed-type hypersensitivity response controlled by T lymphocytes (Smith et al, 1998, *Immunol. Cell Biol.* 76:497–512). Topical corticosteroids are used to control inflammation but are themselves associated with significant complications including cataract, steroid-induced glaucoma and infection.

Corneal graft rejection is another ocular disorder that suffers from a paucity of efficacious treatments. The success rate for corneal transplantation in Australia is 62% at 10 years (Williams et al, 1993, *Aust. NZ. J. Opthalmol.* 21: 1–48). Irreversible rejection is the major cause of corneal graft failure, accounting for at least 30–50% of all cases, and occurs despite universal use of topical glucocorticosteroids (Williams et al, 1993, *Aust. NZ. J. Opthalmol.* 21: 1–48). Adjunctive treatment with systemic immunosuppressants such as cyclosporin A is used occasionally, but probably confers little benefit on graft survival and can be associated with serious morbidity (Williams et al, 1993, *Transplantation Reviews.* 7: 44–64).

Herpetic keratitis is caused by herpes simplex virus infection of the trigeminal ganglia (Streilein et. al. 1997, *Immunol. Today.* 18: 443–9, Hendricks, R. L. 1997, *Cornea.* 16: 503–6). Herpetic eye disease is the most common infectious cause of blindness in developed countries (Streilein et. al. 1997, *Immunol. Today* 18: 443–9) and serious sequelae including pain, iritis, bacterial superinfection, corneal perforation and blindness occur in 3% of affected individuals. Epithelial herpetic disease (e.g. dendritic ulceration) is readily diagnosed by polymerase chain reaction (PCR)-based tests, amongst others, and can be treated reasonably successfully with antiviral agents. Diagnosis and treatment are far more difficult for disciform endotheliitis, or for the stromal disease (e.g. disciform keratitis, irregular stromal keratitis, kerato-uveitus) that occurs in one fifth of patients with ocular herpes. It is unusual to find virus particles in stromal biopsy specimens, and very difficult to culture virus from them. Diagnosis is usually made on clinical grounds and by exclusion. Topical acyclovir is the treatment of choice for herpetic keratitis (although emergence of drug-resistant strains is causing concern) and long-term oral prophylaxis halves the incidence of recurrences (Herpetic Eye Disease Study Group. 1998, *N. Engl. J. Med.* 339: 300–6). However, corneal damage is not prevented by acyclovir. The pathogenesis of epithelial disease results from productive, lytic infection of corneal epithelial cells. In contrast, the pathogenesis of stromal or endothelial cell herpetic disease results from an immune reaction to viral antigen expressed on corneal cells or released into the stroma (Streilein et. al. 1997, *Immunol. Today* 18: 443–9, Hendricks, R. L. 1997 *Cornea* 16: 503–6).

Reference also may be made to acanthamoeba keratitis, a very serious, painful disease that can result in loss of vision in the affected eye. The condition, caused by a common, free-living, soil and freshwater amoeba (Acanthamoeba), was once thought to be rare, but there has been an exponential increase in the number of reported cases over the past 5–10 years. Over 90% of cases have occurred in contact lens-wearers who have not adhered to recommended lens cleaning and disinfection procedures. Of critical importance in achieving a good visual outcome is early diagnosis. In the early stages of infection, amoebae are found in the corneal epithelium where they can be removed by debridement, often without the need for antimicrobial agents (Brooks et al. 1994, *Cornea* 13:186–189). Unfortunately, the diagnosis is often delayed, as the clinical picture can resemble other forms of infectious keratitis, particularly herpetic keratitis. This allows the organisms to invade the corneal stoma where they attack keratocytes (Badenoch et al. 1995, *Int. J. Parasitol.* 25: 229–239) and cause irreversible tissue damage. In this situation, attempting to achieve a laboratory diagnosis by corneal scrapings is usually unsuccessful and deep biopsy, itself damaging, is unreliable.

Immunoglobulins have gained widespread diagnostic and therapeutic application in various medicinal fields. For example, whole monoclonal and/or polyclonal antibodies have been used to suppress transplant rejection, to modulate different autoimmune diseases, to treat neoplasias, and to prevent and treat infectious diseases. Typically, systemic administration of antibodies is required for these purposes, which may cause serious systemic side effects. These side effects have prevented the systemic application of antibodies for treating diseases affecting non-vital organs like the eye. However, there are many ocular diseases such as those described above, where antibody treatment would have advantages.

In view of the above, Whitcup et al (WO 93/06865) disclose the use of monoclonal antibodies against cell adhesion molecules to treat ocular inflammation. In particular, Whitcup et al contemplate administration of such antibodies to the eye by intravenous injection, by intracameral or periocular injection, by surgical implantation of a depot, and by topical administration using eye drops or ophthalmic ointment. Whitcup et al provide enabled methods for parenteral administration of anti-cell adhesion molecule antibodies in an animal model. However, they do not provide any enabled methods for topical administration of such antibodies and are wholly silent on any data establishing the utility of the claimed methods. In fact, the present inventors have found that conventional whole antibodies alone cannot penetrate the cornea or the sclera via topical routes.

Various anatomical barriers relating to the eye may underlie the poor intraocular penetrance of whole antibodies. In this regard, the cornea is the principal barrier to entry of foreign substances. It has two distinct penetration barriers, the corneal epithelium and the corneal stroma (Burstein and Anderson, 1985, *J. Ocul. Pharmacol.* 1(3): 309–26; Maurice D M, 1980, *Int. Ophthalmol. Clin.* 20(3):7–20; and Mishima S, 1981, *Invest. Ophthalmol. Vis. Sci.,* 21(4): 504–41). The corneal epithelium is a major barrier for hydrophilic substances. Hydrophilic molecules less than 350 Da can enter via a paracellular route, but larger hydrophilic molecules are essentially barred. This barrier function can be modulated to an extent by the use of penetration enhancers. The second barrier, the corneal stroma, interferes with penetration of lipophilic drugs and large hydrophilic drugs. The corneal stroma is regularly quoted as being "transparent" to hydrophilic molecules of up to 500 kDa (Bartlett and Jaanus in *Clinical Ocular Pharmacology*). This figure however is contradicted by studies of Olsen et al (1995, *Inv. Ophihal. Vis. Sci* 36(9): 1893–1903) who showed in vitro that human scleral permeability decreased linearly with increasing molecular weight of hydrophilic compounds up to about 40 kDa after which permeability decreased sharply. Comparative studies with bovine and rabbit stroma and sclera suggest that stroma is similar though slightly more transparent (Maurice and Polgar, 1977, *Exp. Eye Res.* 25: 577–582). Accordingly, the finding of Olsen et al (1995, supra) would be expected to apply to human corneal stroma.

Penetration of sclera or stroma of an intact eye by whole IgG occurs very slowly, if at all, regardless of whether application is topical (Pleyer et al 1995, *Invest. Ophthalmol. Vis. Sci.* 36(1): 52–6), subconjunctival (Ososky et al 1993, *Graefes Arch. Clin. Exp. Ophthalmol.* 231(2): 122–128) or systemic (Verhagen et al 1990, *Invest. Ophthalmol. Vis. Sci.* 31(8): 1519–1525). Formulation of whole IgG in a lipid environment e.g., within a liposome, can facilitate transfer across the corneal epithelium (Pleyer et al 1995, supra) but does not resolve the problem of slow passage across the stroma or sclera for molecules of this size.

Despite the encouraging data of Pleyer et al (1995, supra) with liposomal encapsulation, the present inventors have shown that intracameral injection of monoclonal antibodies causes a harmful fibrinous reaction in the anterior chamber of the eye (Williams et al. 1992, *Transplantation,* 54: 38–43). This pro-inflammatory side effect may reflect local complement activation by the Fc-portion of the antibody. The eye contains many non-regenerating structures that are irreversibly damaged by such inflammatory side effects. At least in one reported case, the inflammatory side effect of intraocular antibodies had blinding consequences for the patient (case reported by M. Böhnke, Bern, presented at the international conference on corneal transplantation, Heidelberg, September 1994).

From the foregoing, and despite a long-felt need for intraocular immunotherapeutic strategies, it would appear that antibodies have limited clinical potential for efficacious treatment of ocular disorders.

SUMMARY OF THE INVENTION

The present inventors have discovered that sub-immunoglobulin antigen-binding molecules such as Fv immunoglobulin fragments, minibodies and the like can penetrate the cornea to provide efficacious treatment and/or diagnosis of ocular disorders with markedly reduced side effects.

Accordingly, in one aspect, the invention provides a method of treating an ocular disorder, comprising administering to a patient in need of such treatment, an effective amount of a sub-immunoglobulin antigen-binding molecule that is immuno-interactive with a target antigen associated with the disorder.

In another aspect of the invention, there is provided a method of diagnosing an ocular condition, comprising:

contacting a portion of an eye with a sub-immunoglobulin antigen-binding molecule that is immuno-interactive with a target antigen indicative of the condition; and detecting the presence of a complex comprising the said antigen-binding molecule and the target antigen.

In yet another aspect of the invention there is provided a composition for treatment or diagnosis of an ocular disorder, comprising a sub-immunoglobulin antigen-binding molecule that is immuno-interactive with a target antigen associated with the disorder, together with a carrier.

In a further aspect, the invention resides in an ocular composition comprising a sub-immunoglobulin antigen-binding molecule that is immuno-interactive with a target antigen in the eye.

BRIEF DESCRIPTION OF THE FIGURES

FIG. 14 is a graph showing titration of miniantibody binding activity in eye drops and after penetration in the anterior chamber.

DETAILED DESCRIPTION OF THE INVENTION

1. Definitions

Figure 1:
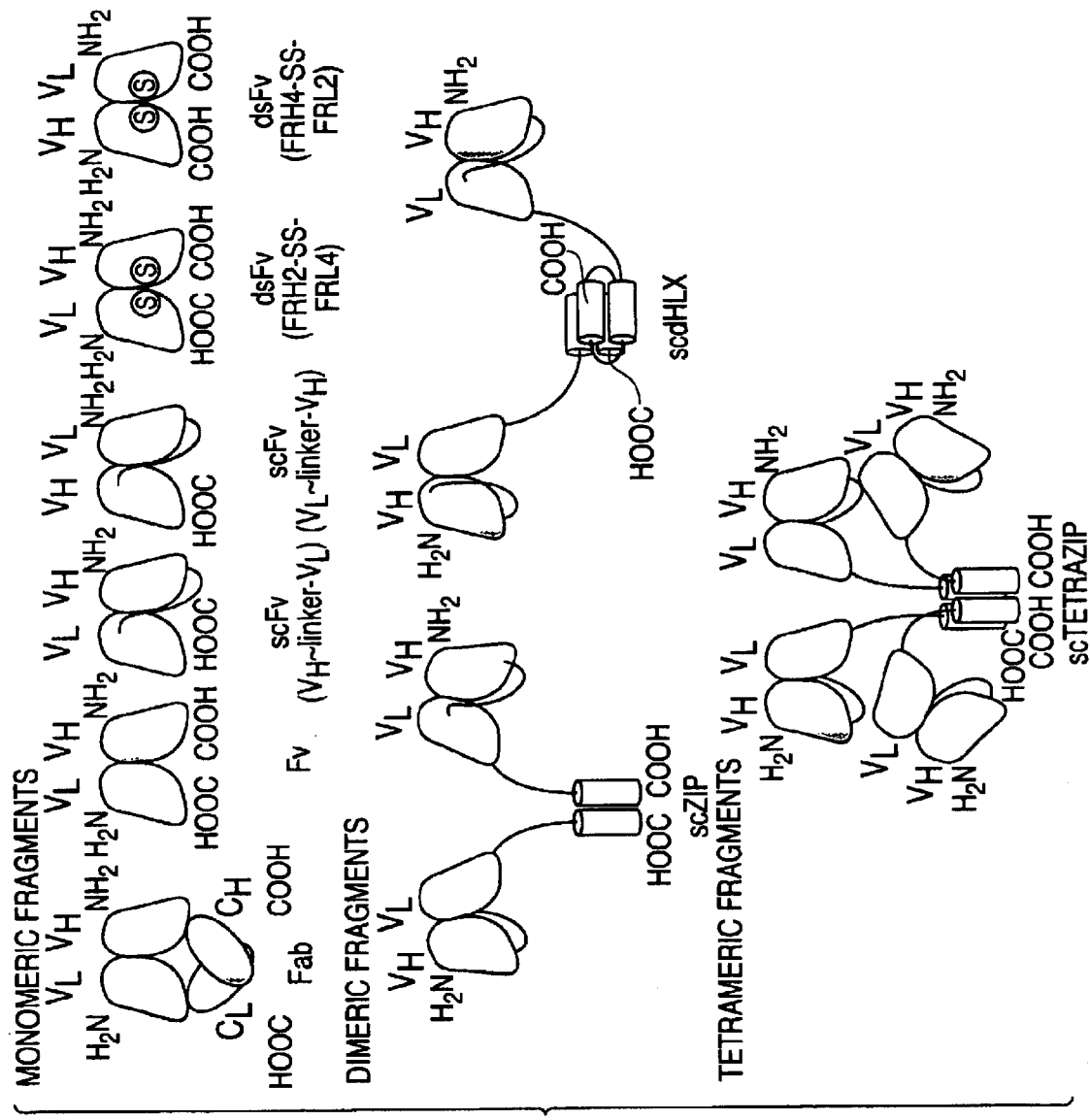
FIG. 1, taken from Plückthun et al (1996, *Antibody engineering: A practical approach.* 203–252), is a schematic representation of sub-immunoglobulin antigen binding molecules suitable for functional high level expression in *E. coli* and for use in accordance with the present invention.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

By "affinity" is meant the strength of the interaction between an individual antigen binding site on an immunoreactive molecule and its corresponding site on the antigen.

By "associated with the disorder" is meant that the target antigen may be linked directly or indirectly with the disorder. For instance, the target antigen may be an epitope of a signal molecule that indirectly causes, contributes to or is indicative of the ocular disorder.

The term "diagnosis" is used herein in its broadest sense to include detection of an antigen reactive to a sub-immunoglobulin antigen-binding molecule. Also included within its scope, is the analysis of disorder mechanisms associated with ocular disorders. Accordingly, the term "diagnosis" includes the use of sub-immunoglobulin antigen binding molecules for research purposes as tools to detect and understand mechanisms associated with ocular disorders.

The term "effective amount" as used herein is an amount of sub-immunoglobulin antigen binding molecule that will treat or prevent an ocular disorder. The effective amount may be an amount that can inhibit an action of a target antigen for which the sub-immunoglobulin antigen-binding molecule is reactive thereagainst. Methods of inhibiting an action may include saturating the target antigen in the eye with a sub-immunoglobulin antigen-binding molecule thereby neutralising the target antigen.

Reference herein to "immuno-interactive" includes reference to any interaction, reaction, or other form of association between molecules and in particular where one of the molecules is, or mimics, a component of the immune system.

The term "ocular condition" is used herein to describe any condition of the eyes. It may include a healthy condition or an unhealthy condition such as a disorder of the eye (ocular disorder).

The term "patient" refers to patients of human or other animal origin and includes any individual it is desired to examine or treat using the methods of the invention. However, it will be understood that "patient" does not imply that symptoms are present.

By "pharmaceutically acceptable carrier" is meant a solid or liquid filler, diluent or encapsulating substance that may be safely used in systemic administration.

By "sub-immunoglobulin antigen binding molecule" is meant a molecule that is smaller than an immunoglobulin molecule and has binding affinity for a target antigen. It will be understood that this term extends to non-immunoglobulin derived protein frameworks which exhibit antigen binding activity. It will also be understood that this term is not limited by the source from which any nucleotide sequence encoding the said antigen-binding molecule is obtained, or by the source from which the said antigen-binding molecule is expressed or isolated.

By "target antigen" is meant an antigen that is associated with an ocular disorder for which treatment or diagnosis is sought.

The term "treating" is used herein in its broadest sense to include both therapeutic and prophylactic (i.e., preventative) treatment designed to ameliorate the ocular disorder.

Throughout this specification, unless the context requires otherwise, the words "comprise ", "comprises" and "comprising" will be understood to imply the inclusion of a stated integer or group of integers but not the exclusion of any other integer or group of integers.

2. Sub-immunoglobulin Antigen Binding Molecules

The subject invention stems from the unexpected discovery that sub-immunoglobulin antigen-binding molecules can penetrate the cornea to significant levels when applied topically to the eye. In light of this discovery, the present inventors believe that penetrance of such molecules into the eye can also be achieved by alternate routes including parenteral administration and periocular injection.

To allow treatment of ocular disorders, it is preferable that sub-immunoglobulin antigen-binding molecules of the invention fulfil the following conditions. Firstly, it is desirable that they should allow for application to the eye to avoid or at least partially alleviate some systemic side effects. A second condition is that these binding molecules must not cause any potentially harmful pro-inflammatory side effects inside the eye.

Suitable sub-immunoglobulin antigen binding molecules include, but are not restricted to, Fv, Fab, Fab' and F(ab')$_2$ immunoglobulin fragments. Preferably, the sub-immunoglobulin antigen-binding molecule does not comprise the Fc portion of an immunoglobulin molecule.

Preferably, the sub-immunoglobulin antigen-binding molecule comprises a synthetic Fv fragment. Suitably, the synthetic Fv fragment is stabilised. Exemplary synthetic stabilised Fv fragments include single chain Fv fragments (sFv, frequently termed scFv) in which a peptide linker is used to bridge the N terminus or C terminus of a $V_H$ domain with the C terminus or N-terminus, respectively, of a $V_L$ domain. ScFv lack all constant parts of whole antibodies and are not able to activate complement. Suitable peptide linkers for joining the $V_H$ and $V_L$ domains are those which allow the $V_H$ and $V_L$ domains to fold into a single polypeptide chain having an antigen binding site with a three dimensional structure similar to that of the antigen binding site of a whole antibody from which the Fv fragment is derived. Linkers having the desired properties may be obtained by the method disclosed in U.S. Pat. No. 4,946,778, the disclosure of which is incorporated herein by reference. However, in some cases a linker is absent. Exemplary synthetic Fv fragments are illustrated in FIG. 1.

ScFvs may be prepared, for example, in accordance with methods outlined in Kreber et al (Krebber et al. 1997, J. Immunol. Methods; 201(1): 35–55), the disclosures of which are incorporated herein by reference. Alternatively, they may be prepared by methods described in U.S. Pat. No. 5,091,513, European Patent No 239,400 or the articles by Winter and Milstein (1991, *Nature* 349:293) and Plückthun et al (1996, In *Antibody engineering: A practical approach.* 203–252), which are incorporated herein by reference.

Alternatively, the synthetic stabilised Fv fragment comprises a disulphide stabilised Fv (dsFv) in which cysteine residues are introduced into the $V_H$ and $V_L$ domains such that in the fully folded Fv molecule the two residues will form a disulphide bond therebetween. Suitable methods of producing dsFv are described for example in (Glockscuther et al. *Biochem.* 29: 1363–1367; Reiter et al. 1994, *J. Biol. Chem.* 269: 18327–18331; Reiter et al. 1994, *Biochem.* 33: 5451–5459; Reiter et al. 1994. *Cancer Res.* 54: 2714–2718; Webber et al. 1995, *Mol. Immunol.* 32: 249–258), which are incorporated herein by reference.

Also contemplated as sub-immunoglobulin antigen binding molecules are single variable region domains (termed dAbs) as for example disclosed in (Ward et al. 1989, *Nature* 341: 544–546; Hamers-Casterman et al. 1993, *Nature.* 363: 446–448; Davies & Riechmann, 1994, *FEBS Lett.* 339: 285–290), which are incorporated herein by reference.

Suitably, the sub-immunoglobulin antigen-binding molecule is a "minibody". In this regard, minibodies are small versions of whole antibodies, which encode in a single chain the essential elements of a whole antibody. Suitably, the minibody is comprised of the $V_H$ and $V_L$ domains of a native antibody fused to the hinge region and CH3 domain of the immunoglobulin molecule as, for example, disclosed in U.S. Pat. No. 5,837,821, which is incorporated herein by reference.

In an alternate embodiment, the sub-immunoglobulin antigen binding molecule may comprise non-immunoglobulin derived, protein frameworks. For example, reference may be made to (Ku & Schultz, 1995, *Proc. Natl. Acad. Sci. USA,* 92: 652–6556) which discloses a four-helix bundle protein cytochrome b562 having two loops randomised to create complementarity determining regions (CDRs), which have been selected for antigen binding.

The sub-immunoglobulin antigen-binding molecule may comprise a modifying moiety. In one form, the modifying moiety may modify the effector function of said molecule. For example, the modifying moiety may comprise a peptide for detection of said antigen-binding molecule, for example in an immunoassay. Alternatively, the modifying moiety may facilitate purification of said antigen binding molecule. In this instance, the modifying moiety includes, but is not limited to, glutathione-S-transferase (GST), maltose binding protein (MBP) and hexahistidine ($HIS_6$), which are particularly useful for isolation of the antigen-binding molecule by affinity chromatography. For the purposes of purification by affinity chromatography, relevant matrices for affinity chromatography are glutathione-, amylose-, and nickel- or cobalt-conjugated resins respectively as is well known in the art. The modifying moiety may comprise a therapeutic agent to be targeted to at least a portion of the eye. Alternatively, the modifying moiety may comprise an enzyme such as an enzyme of potential therapeutic benefit e.g., fibrolytic agents (Holvoet et al., 1991, *J. Biol. Chem.* 366: 19717–19724; Yang et al. 1994, *Biochem.* 33: 606–612) or prodrug activators (Bosslett et al., 1992, *Br. J. Cancer,* 65: 234–238; Goshorn et al., 1993, *Cancer Res.,* 53: 2123–2127; Rodrigues et al., 1995, *Cancer Res.,* 55: 63–70) and enzymes capable of driving colorimetric assays for use in immunoassays. In another form, the modifying moiety may increase intraocular penetrance of said antigen-binding molecule. In this instance, the modifying moiety may comprise a lipid moiety or lipid tail as for example described by Barr et al (1998, *Adv. Drug Delivery Reviews* 32: 247–271, incorporated herein by reference). Alternatively, the modifying moiety may comprise the HIV tat protein as described for example by Schwarze et al (1999, *Science* 285: 1569–1572), which is incorporated herein by reference.

The sub-immunoglobulin antigen binding molecule may be multivalent (i.e., having more than one antigen binding site) providing it is capable of penetration into the eye when administered parenterally or topically or injected into the subconjunctival, peri- or retrobulbar space, or injected directly into the eye. Such multivalent molecules may be specific for one or more antigens. Multivalent molecules of this type may be prepared by dimerisation of two antibody fragments through a cysteinyl-containing peptide as, for example disclosed by (Adams et al., 1993, *Cancer Res.* 53: 4026–4034; Cumber et al., 1992, *J. Immunol.* 149: 120–126), which are incorporated herein by reference. Alternatively, dimerisation may be facilitated by fusion of the antibody fragments to amphiphilic helices that naturally dimerise (Pack P. Plünckthun, 1992, *Biochem.* 31: 1579–1584, incorporated herein by reference), or by use of domains (such as the leucine zippers jun and fos) that preferentially heterodimerise (Kostelny et al., 1992, *J. Immunol.* 148: 1547–1553, incorporated herein by reference). In an alternate embodiment, the multivalent molecule may comprise a multivalent single chain antibody (multi-scFv) comprising at least two scFvs linked together by a peptide linker. In this regard, non-covalently or covalently linked scFv dimers termed "diabodies" may be used. Multi-scFvs may be bispecific or greater depending on the number of scFvs employed having different antigen binding specificities. Multi-scFvs may be prepared for example by methods disclosed in U.S. Pat. No. 5,892,020, which is incorporated herein by reference.

3. Compositions

The invention also extends to a composition for use in treatment or diagnosis of an ocular disorder wherein the composition comprises a sub-immunoglobulin antigen-binding molecule that is immuno-interactive with a target antigen associated with the disorder, together with a carrier.

The carrier is preferably a pharmaceutically acceptable carrier. Depending upon the particular route of administration, a variety of pharmaceutically acceptable carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

Any suitable route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Preferably, a parenteral or topical route is employed. Alternatively, the composition is suitably administered by injection into the subconjunctival, peribulbar or retrobulbar space.

Dosage forms include tablets, dispersions, suspensions, injections, solutions, syrups, troches, capsules, and suppositories, aerosols, collagen shields, transdermal patches and the like. These dosage forms may also include injecting or implanting controlled releasing devices designed specifically for this purpose or other forms of implants modified to act additionally in this fashion. Controlled release of said antigen binding molecule may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by use of other polymer matrices, liposomes and/or microspheres.

Pharmaceutical compositions of the present invention suitable for oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more immunogenic agents as described above with the carrier which constitutes one or more necessary ingredients. In general, the compositions are prepared by uniformly and intimately admixing the antigen binding molecule of the invention with liquid carriers or finely divided solid carriers or both, and then, if necessary, shaping the product into the desired presentation.

The above compositions may be administered in a manner compatible with the dosage formulation, and in such amount as is therapeutically effective to alleviate patients from ocular disorder. The dose administered to a patient, in the context of the present invention, should be sufficient to effect a beneficial response in a patient over time such as a reduction or cessation of blood loss. The quantity of the antigen binding molecule(s) to be administered may depend on the subject to be treated inclusive of the age, sex, weight and general health condition thereof. In this regard, precise amounts of the antigen binding molecule(s) for administration will depend on the judgement of the practitioner. In determining the effective amount of the antigen-binding molecule to be administered in the treatment of an ocular disorder, the physician may evaluate the progression of the disorder over time. In any event, those of skill in the art may readily determine suitable dosages of the antigen-binding molecule of the invention. Such dosages may be in the order of nanograms to milligrams of the antigen-binding molecule.

The composition suitably includes a penetration enhancer such as benzalkonium chloride, digitonin, dihydrocytochalasin B, capric acid, increasing pH from 7.0 to 8.0. Preferably, the penetration enhancer is directed to enhancing penetration of the antigen binding molecule(s) through the corneal epithelium.

Suitably, the composition includes liposomes in which the antigen-binding molecules of the invention are encapsulated. Any suitable procedure of liposome encapsulation of active is contemplated. In this regard, exemplary methods are disclosed by Frasta et al (1999, *J. Pharm. Pharmacol.* 51(5): 565–576) and Masuda et al (1996, *Invest. Ophthalmol. Vis. Sci.* 37(9): 1914–1920), which are incorporated herein by reference.

The half-life of the antigen-binding molecule of the invention may be prolonged by any suitable procedure if desired. Preferably, such molecules are chemically modified with polyethylene glycol (PEG), including monomethoxypolyethylene glycol, as for example disclosed by Chapman et al (1999, *Nature Biotechnology* 17: 780–783), which is incorporated herein by reference.

Suitable target antigens include, but are not limited to, an MHC molecule including MHC molecules that are class I- or class II-restricted, a co-stimulatory molecule (e.g., CD80, CD86 and CD152), an adhesion molecule (e.g., CD11b/e, CD18, CD54 and CD62L), a receptor-associated molecule (e.g., CD3, CD4, CD8, CD28, CD40, CD40L and CTLA4), a cytokine receptor (e.g., the interleukin 2 receptor (IL-2R), or subunit thereof such a CD25, and the interferon γ receptor (IFN-γR) and a viral surface antigen (e.g., gD2 and gB2 antigen of herpes simplex virus or a surface antigen of the herpes virus causing herpetic keratitis).

The invention also provides an ocular composition comprising a sub-immunoglobulin antigen-binding molecule that is immuno-interactive with a target antigen in the eye.

4. Methods of Administration

A further feature of the invention is a method of treating an ocular disorder comprising administering to a patient in need of such treatment an effective amount of a sub-immunoglobulin antigen binding molecule that is immuno-interactive with a target antigen associated with the disorder.

The ocular disorder may be any disease or disorder associated with the eye. Generally the disorder will be a disease of the eye which directly affects the eye. Diseases or disorders associated with the eye may be those diseases or disorders that originate from other parts of the body and that indirectly affect the eye as a side effect of the main disease or disorder.

Typical disease or disorders include corneal graft rejection, uveitis, any ocular infection, inflammatory and infectious diseases such as viral (e.g., herpetic keratitis and adenoviral), bacterial or chlamydial conjunctivitis, ocular tumours, neovascular proliferative diseases such as diabetic retinopathy, neovascular maculopathies, rheumatoid corneal melting disorders or autoimmune disorders such as ocular penthigoid.

The method includes administering an effective amount of the sub-immunoglobulin antigen-binding molecule to the patient. The sub-immunoglobulin antigen binding molecule may be administered locally, either topically to a portion of the eye or be injected into the eye for instance into the subconjunctivital, peri- or retrobulbar space or directly into the eye. Alternatively, said antigen binding molecule may be administered systemically by parental administration.

It is most preferable that said antigen-binding molecule is applied to the eye topically and as an eye drop. The eye drop may be applied to the cornea (clear part in the centre of the eye) thereby allowing the molecules to permeate into the eye. For the treatment of a disease affecting the posterior of the eye, it may be most desirable that the antigen-binding molecule penetrates the sclera when injected under the conjunctiva or around the globe.

The administering of the antigen-binding molecule may be performed after a preliminary step of modulating the surface of the eye to improve penetration of the molecules. Preferably, the epithelial layer such as the corneal epithelium is modulated by a penetration enhancer to allow for a sufficient and rapid penetration of the molecules as for example described above.

Alternatively, the step of administration is characterised by subjecting at least a portion of the eye to iontophoresis such that the antigen-binding molecule penetrates into a desired intraocular region. Suitable methods that may be employed in this regard include those disclosed, for example, by Behar-Cohen et al (1998, *Invest. Ophthalmol. Vis. Sci.* 39(6): 897–904), and Frucht-Pery et al (1996, *Graefes Arch. Clin. Exp. Ophthalmol.* 234(12): 765–9), which are incorporated herein by reference.

The portion of the eye into or onto which the antigen-binding molecule is preferably administered is the portion that allows for penetration of the antigen binding molecule. As described above, administration is preferably performed on the cornea and conjunctiva or the substance may be injected into the subconjunctival, peri- or retrobulbar space to reach the inside of the eye after penetration through the sclera.

5. Methods of Diagnosis

The invention also extends to a method of diagnosis of an ocular condition, comprising contacting a portion of an eye with a sub-immunoglobulin antigen binding molecule that is immuno-interactive with an antigen indicative of the condition, and detecting the presence of a complex comprising the sub-immunoglobulin antigen binding molecule and the antigen.

In a preferred aspect, the invention provides a method of diagnosis of an ocular disorder, comprising contacting a portion of an eye with a sub-immunoglobulin antigen binding molecule that is immuno-interactive with an antigen associated with the disorder, and detecting the presence of a complex comprising the sub-immunoglobulin antigen binding molecule and the antigen.

The antigen that is indicative of the condition may be an antigen that is associated directly or indirectly with the ocular condition. It may be a target antigen or an antigen of a molecule that results as a by-product of the ocular condition.

The presence or absence of the target antigen in the eye may be determined by administering the antigen binding molecule to the eye as for example described in Section 4 above. Preferably, the antigen-binding molecule is administered to the eye as an eye drop or by periocular injection.

Detection of the complex is subsequently determined. Any suitable technique for determining formation of the complex may be used. For example, a sub-immunoglobulin antigen-binding molecule according to the invention having a detectable label associated therewith may be utilised in immunoassays applicable to in vivo detection of target antigen. Immunoassays may include competitive assays as understood in the art.

The label associated with the antigen-binding molecule may include the following:

(i) direct attachment of the label to the antigen-binding molecule;

(ii) indirect attachment of the label to the antigen binding molecule; i.e., attachment of the label to another assay reagent which subsequently binds to the antigen binding molecule; and (iii) attachment to a subsequent reaction product of the antigen binding molecule. The label may be selected from a group including a chromogen, a catalyst, an enzyme, a fluorochrome, a chemiluminescent molecule, a lanthanide ion such as Europium ($Eu^{34}$), a radioisotope and a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes suitable for use as labels is disclosed in United States Patent Specifications U.S. Pat. Nos. 4,366,241, 4,843,000, and 4,849,338, all of which are incorporated herein by reference. Suitable enzyme labels useful in the present invention include alkaline phosphatase, horseradish peroxidase, luciferase, β-galactosidase, glucose oxidase, lysozyme, malate dehydrogenase and the like. The enzyme label may be used alone or in combination with a second enzyme that is in solution.

Suitably, the fluorochrome is selected from a group including fluorescein isothiocyanate (FITC), tetramethylrhodamine isothiocyanate (TRITL) or R-Phycoerythrin (RPE).

A preferred isotope for imaging applications is $^{99m}Tc$, because of its physical properties, cost availability and safety. In order to facilitate labelling with this radiometal, antigen-binding molecules such as scFv have been fused with a short peptide designed to chelate $^{99m}Tc$ within a $N_3S$ co-ordination site (Huston et al., 1996, *Quarterly Journal of Nuclear Medicine*, in press; George et al., 1995, *Proc. Natl. Acad. Sci. USA*, 92: 8358–8363). The resulting molecule is readily labelled in a single step reaction, yielding a highly stable product that retains the immnogenicity of the original scFv.

The present invention will now be more fully described with reference to the following examples. It should be understood, however, that the description following is illustrative only and should not be taken in any way as a restriction on the generality of the invention described above.

EXAMPLES

Example 1

Intraocular Penetration of scFv Antibody Fragments and Divalent Miniantibodies

Engineering and Expression of scFv Antibody Fragments and Divalent Miniantibodies Starting material for the antibody engineering was OX38, a hybridoma cell line that produces whole antibodies with binding specificity against rat CD4 antigen. The engineering process for the scFv antibody fragment followed exactly a technique described by Kreber et al (1997, *J Immunol Methods* 201(1): 35–55) and Plückthun et al (*Producing antibodies in Escherichia coli: from PCR to fermentation*. In: McCafferty J, Hoogenboom H, Chiswell D, eds. *Antibody engineering: A practical approach*. Oxford: Oxford University Press, 1996:203–252. (Hames B, ed. The practical approach series)). In brief, mRNA was extracted from a growing hybridoma cell line and the mRNA was reverse transcribed into cDNA. The genetic information for the variable part of the light and the heavy chain of the antibody was separately amplified by polymerase chain reactions (PCR) using an extended primer set as described by Kreber et al (supra) and Plückthun et al (supra). The DNA products for both chains were spliced together and inserted into the pAKI100 vector that was used to transform *E. coli* JM83 (gift from A. Plückthun). ScFv fragments were expressed in *E. coli* and collected from the culture supernatant. These fragments were tested for their binding activity in a flow cytometer using rat thymocytes as a source of the rat CD4 antigen.

For large-scale production, the insert coding for a functional scFv was cut out of the pAKI100 vector and integrated into a pHB400 vector that was derived from integrating the skp co-expression cassette from vector pHB110 (Bothmann et al., 1998, *Nat. Biotechnol.* 16(4): 376–80) into the vector pAK400 (Kreber et al. supra). The vector pHB400 contains a strong translation initiation region (Shine-Dalgarno SDT7g10 sequence) for optimised scFv expression, a 6-histidine tag for purification by an immobilised metal ion-affinity chromatography (IMAC) and a cassette for co-expression of skp, a chaperon that improves correct scFv folding in the periplasmic space.

For the expression of scFv fragments as divalent miniantibodies, the insert with the scFv sequence was ligated into vector pHB540, which vector was constructed by adding the scFv dimerisation cassette from pAK500 (Kreber et al, supra) into vector pHB400. By this means, scFv fragments can be expressed with an additional double helix motif derived from an antibody hinge region that allows two monovalent fragments to dimerise non-covalently to form a divalent miniantibody with a size of 66 kDa.

Fermentation of E. coli

E coli HB2151 or E. coli BL21 were transformed with the above vectors for scFv or miniantibody expression. Bacterial cultures were grown in a 20 L bench-top fermenter similar to the one described by Plückthun et al (supra) using terrific broth complex medium. Cultures were induced for protein expression at 25° C. and an optical density ($OD_{600\ nm}$) of 20 by addition of 0.1 mM IPTG (isopropyl β-D-thiogalactopyranoside). After three to four hours of expression, cultures were harvested in a Beckman J21 centrifuge (4000×g for 25 min at 4° C.) and bacterial pellets either processed immediately or stored at −70° C.

Purification of scFv and Miniantibodies

To obtain correctly folded and functional scFv or miniantibodies, the bacterial pellets were resuspended in 50 mM sodium borate (NaBo), 0.15 M NaCl, pH 8.0 using 2 mL extraction buffer per gram of pellet and bacteria disrupted by sonication in a Manton-Gaulin flow-through homogeniser. The lysate was centrifuged at 13,000×g for 30 min at 4° C. before the scFv or miniantibody-containing supernatant was passed through a 0.2 μm filter and supplemented with 1% Triton X-100, 1% Tween-20 and 20 mM imidazole. The clarified lysate was loaded onto an IMAC column with nickel-nitrilotriacetic acid (Ni-NTA) resin (Qiagen. QIAexpressionist. Qiagen, Germany, 1999). The column was washed with 20 column volumes (CV) of equilibration buffer (50 mM NaBo, 1% Triton X-100, 1% Tween-20, 20 mM imidazole, pH 8.0) and 5 CV of 50 mM NaBo, 20 mM imidazole, pH 8.0. Bound protein was eluted from the column using a linear 20–500 mM imidazole gradient over 10 CV. Protein-containing fractions were pooled and loaded onto a Q-Sepharose-HP anion exchange column and equilibrated with 20 mM HEPES buffer (N-[2-hydroxyethyl]piperazine-N'-[4-butanesulfonic acid]), pH 8.0. Unbound protein was washed with 3 CV of equilibration buffer before bound protein was eluted in 20 mM HEPES pH 8.0 with a linear 0–1 M NaCl gradient over 7 CV. Fractions containing the purified scFv or miniantibodies were pooled, sterile filtered and dialysed against 2×150 volumes of 20 mM HEPES pH 8.0, 0.15 mM NaCl at 4° C. Samples were taken along the purification process and analysed using SDS-PAGE (sodium dodecyl sulfate polyacrylamide gel electrophoresis). In a preferred embodiment, the purified molecules are chemically modified with monomethoxy-polyethylene glycol (PEG) using the procedure of Chapman et al (1999, *Nature Biotechnology* 17: 780–783) to prolong their half-life.

Testing scFv for Antigen Binding

All testing on scFv fragments for antigen binding were performed by flow cytometry on rat thymocytes. Thymocyte cell suspensions were prepared by standard protocols on freshly harvested rat thymus tissue. Thymocytes ($5\times10^5$) suspended in 50 μL RPMI culture medium were used per assay tube. High sensitivity flow cytometric assays were carried out at 4° C. using 30 minutes incubation steps for scFv (50 μL sample), anti-poly-His mouse antibody (50 μL diluted 1:200, Sigma), biotinylated goat anti-mouse antibody (50 μL diluted 1:50, Vector) and Streptavidin R-Phycoerythrin conjugate (50 μL diluted 1:50, Sigma). Cells were washed with 30 volumes of PBS-azide in between incubations. Assays were fixed by adding 50 μL fixative (PBS, 0.5% formaldehyde) and read in a flow cytometer.

Corneal Penetration Experiments

Corneal Tissue

Penetration of scFv, miniantibodies and whole IgG antibodies was tested in eyes of normal 8–14 months old pigs that were killed for human consumption at a local abattoir 2–5 hours prior to the experiments. A single human eye that was not suitable for clinical use in transplantation was obtained from the local eye bank and used within 2 hours after enucleation. Four corneas from cats that were housed and killed at the animal house of the Institute for Medical and Veterinary Sciences (Adelaide, SA) for other experimental reasons were used within 3 hours of enucleation.

Corneo-scleral buttons were dissected using standard eye bank techniques. Special care was taken to prevent distortion of the corneas during tissue preparation or mounting onto the chambers, as this might affect the integrity of the barrier function. In those eyes that were used to investigate only stromal penetration, the corneal epithelium was carefully removed with a no. 11 scalpel and a dry cotton bud before preparation of the cornea-scleral button.

Corneal Penetration Set-ups

Corneal Perfusion Chambers

Figure 2:
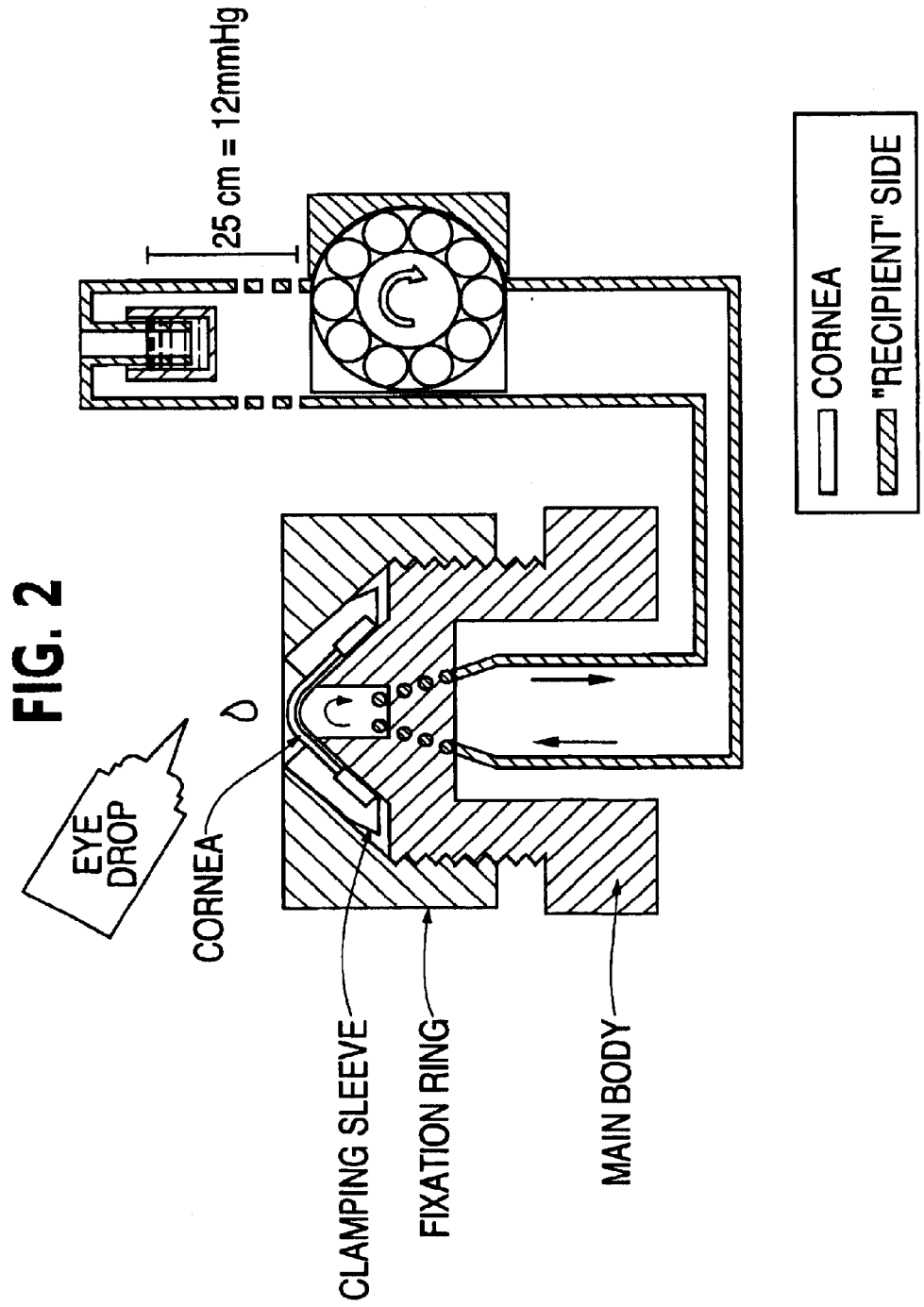
FIG. 2 illustrates a corneal perfusion chamber: A corneoscleral button is dissected and tightly clamped into the perfusion chamber. A fine thread allows clamping adjustment without the risk of tissue damage. The fluid on the "recipient" corneal side circulates continuously. The total fluid volume is 3.5–4 mL. The elevated chamber outflow into the reservoir causes a positive pressure inside the chamber mimicking physiological ocular conditions.

In vitro penetration of scFv through cat and pig corneas was studied in a corneal perfusion chamber (FIG. 2). The perfusion chamber consists of 3 parts: the main body, a clamping sleeve and a fixation ring, all parts made out of polycarbonate (manufactured by the Centre of Biomedical Engineering, Flinders Medical Centre, Adelaide). The "shoulders" of the main body that form the posterior side of the clamp are angled by 30° to support the natural curvature of corneas from different species such as human, pigs and cats. The central cavity that forms together with the mounted cornea the chamber on the receiving side, is 12 mm in diameter and 3 mm in depth. The main body also harbours the channels for in- and outflow for the perfusion lines. The clamping sleeve that clamps the cornea from the epithelial side to the main body has two stainless steel guide pins to direct the vertical movement without twisting, to prevent possible sheer stress and edge damage to the cornea during assembly. The clamping sleeve also contains a fluid channel through which applied eye drops can be sucked off, mimicking lacrimal drainage. The cornea and the clamping sleeve on its surface are pressed against the main chamber body by the fixation ring, which has a fine thread (1-mm pitch) to allow a very precise adjustment of clamping power. Once the cornea is mounted properly, the whole chamber is attached to a heat exchange block through which warm water is circulating from a water bath.

Assessment of Corneal Tissue

Tissue viability was routinely assessed every 30 min during all experiments by measuring corneal thickness with a hand-held pachymeter (BVI pocket pachymeter, B.V. International, 63100 Clermont-Ferrand, France). At the beginning of each experiment the corneas were perfused for one hour and 3 or more different measurements during the second 30 minutes established baseline values of the corneal thickness. An increase in thickness of more than 10% from baseline values during the subsequent experiments was regarded as endothelial dysfunction and the cornea was discarded.

The experimental drugs such as scFv, miniantibodies, whole IgG antibodies or fluorescein, in a pure form or supplemented with different penetration enhancers, were administered as eye drops every 20 to 30 minutes to the epithelial side of the cornea. On the recipient side of the cornea, the perfusion chamber formed an artificial intraocular space that was filled with BSS-Plus (Alcon). The total volume of the BSS-Plus solution that continuously circulated through the artificial eye and the reservoir was 4 mL. Elevating the solution reservoir 25 cm above the level of the artificial eye created a positive pressure of 12 mmHg inside the chamber, simulating physiological conditions (FIG. 2).

To assess drug penetration, hourly samples of 100 μL were taken from the circulating fluid on the recipient side and replaced by the same volume of fresh BSS-Plus. ScFv, miniantibody and whole IgG antibody penetration was determined by standard fluorocytometry (Zola et al, 1990, *J Immunol Methods* 135(1–2): 247–55) using rat thymocytes as a CD4-antigen source and a mouse anti-polyHIS-tag secondary antibody (Sigma). Penetration of sodium fluorescein was assessed by measuring absorption at 493 nm using an ELISA reader with the appropriate filters.

Whole Eye Penetration Set-up

Figure 3:
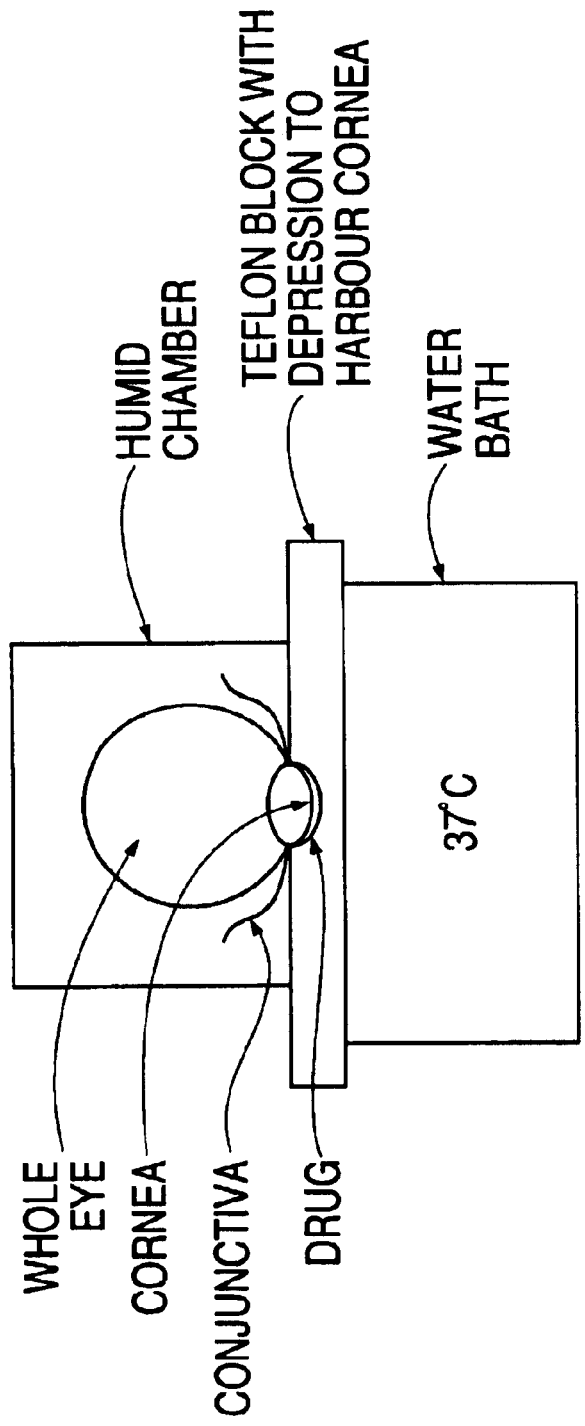
FIG. 3 illustrates a chamber adapted for measuring penetrance of a drug into whole human or pig eyes. Whole eyes with intact conjunctival tissue are positioned onto the Teflon block such that the cornea is harboured within a well formed in the Teflon block. The well is filled with the drug such that the cornea is the only tissue in contact with the drug. The whole eye is covered with an inverted plastic container to form a humid chamber and the set-up is placed above a water bath to keep the eye at a temperature of 35–37° C.

Whole human or pig eyes with intact conjunctival tissue were positioned onto a Teflon block with a depression tooled into the Teflon surface, such that the downward facing cornea could be placed into a well (FIG. 3). The well was partly filled with 100 μL of scFv or miniantibodies. Care was taken that no other tissue except the cornea came in contact with the drug. The whole eye was covered with an inverted plastic container to form a humid chamber and the set-up was placed above a water bath to keep the eye at a temperature of 35–37° C. At the end of the incubation period, the whole globe was washed several times with BSS, dried with a paper tissue and washed again. Samples of anterior chamber fluid were collected with a 27G syringe needle that was passed through the cornea into the anterior chamber. The concentration of penetrated scFv and miniantibody was assessed in a FACS assay as in the perfusion chamber set-up.

At the end of all experiments, corneas were fixed in buffered formalin (10% formalin in PBS) and embedded in paraffin. Standard 10 μm sections were stained with PAS and examined under a microscope.

Results

ScFv and Miniantibody Purification

The eluate from the nickel-NTA purification column had a protein concentration of 0.5 mg/mL with purity of 52% for the OX38 scFv and a protein concentration of 0.74 mg/mL with purity of 21% for the OX38 miniantibody respectively. The subsequent purification over a Q-Sepharose™ anion exchange column resulted in a final scFv concentration of 3.98 mg/mL with a purity of 98% and a miniantibody concentration of 1.83 mg/mL and a purity of 75%. The two step purification protocol over a nickel and a subsequent ion exchange column resulted in a clinical grade purity with endotoxin levels of only 1.08 endotoxin units (EU)/mg of scFv and 36 EU/mg of miniantibodies.

After the first purification step over the nickel column, the main contaminants in the scFv batch were rotamase (peptidyl-propyl cis-trans isomerase SLYD) and the histone-like protein HLP1. Rotamase is a histidine-rich protein that has likely co-purified independently of the scFv fragments on the nickel column. It was effectively removed by the subsequent purification over the Q-Sepharose column. The second contaminant HLP1 contains neither histidine, cysteine nor tryptophan. It was therefore hypothesised that HLP1 was attached to either the scFv or to rotamase to permit its co-purification in the nickel column. Based on HLP1 having an isoelectric point of 9.5, we expected this contaminant to be removed by Q-Sepharose™ anion exchange chromatography at pH 8.0. However HPL1 was also found in the final product after this chromatographic step, indicating that it must have been carried through the purification process bound to a portion of the OX38 scFv fragment. HLP 1 has a size of 15.6 kDa increasing the effective size of contaminated scFv molecules to 43 kDa.

The scFv fragments used for penetration experiments in this study were purified over a nickel column only with a final scFv concentration of 0.2–0.25 mg/mL. The miniantibodies used for the penetration experiment underwent the full two-step purification protocol with a final miniantibody concentration of 1.8 mg/mL.

ScFv Specificity for Rat CD4 Antigen

Figure 4:
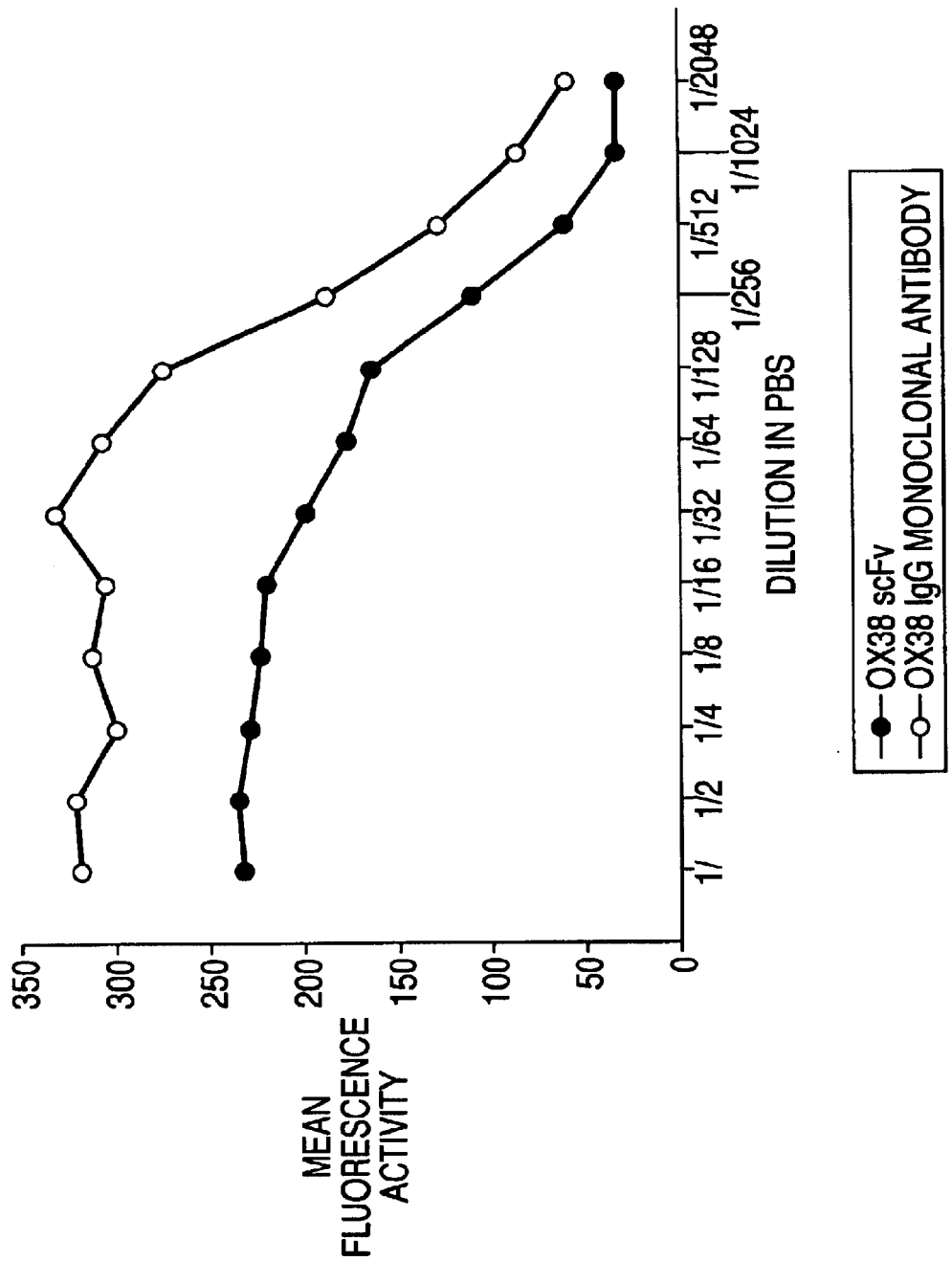
FIG. 4 is a graph showing antigen-binding activity measured in a flow cytometry assay. The scFv shows concentration dependent binding to its target antigen, with a pattern similar to that obtained with the whole antibody.

ScFv binding to rat CD4 antigen was tested in a flow cytometry assay using rat thymocytes. Greater than 95% of all thymocytes expressed CD4 antigen on their surface as shown in a flow cytometry assay with OX38, a whole monoclonal antibody. OX38 binds specifically to rat CD4. The CHRI-r4-Fv1 scFv bound in an identical manner to all thymocytes. The maximal fluorescence intensity of samples with CHRI-r4-Fv1 scFv was about two-thirds the intensity found with OX38. However, the fluorescence intensity in dilution series decreased in an identical pattern in OX38 antibodies and CHRI-r4-Fv1 scFv, indicating similar binding properties (FIG. 4).

To exclude CD4-independent or non-specific binding of CHRI-r4-Fv1 scFv to cell membranes, flow cytometry assays with Jurkat cells (a human T-cell line) and J5.CD4 (transfected Jurkat cell line that expressed full length rat CD4 on its surface) were performed. CHRI-r4-Fv1 scFv did not exhibit any non-specific binding as shown by negative flow cytometry assays using Jurkat cells. Binding specificity to rat CD4 was proven in a flow cytometry assay on transfected J5.CD4, where scFv bound in a similar manner as OX38.

Corneal Penetration of scFv (28 kDa)

Figure 5:
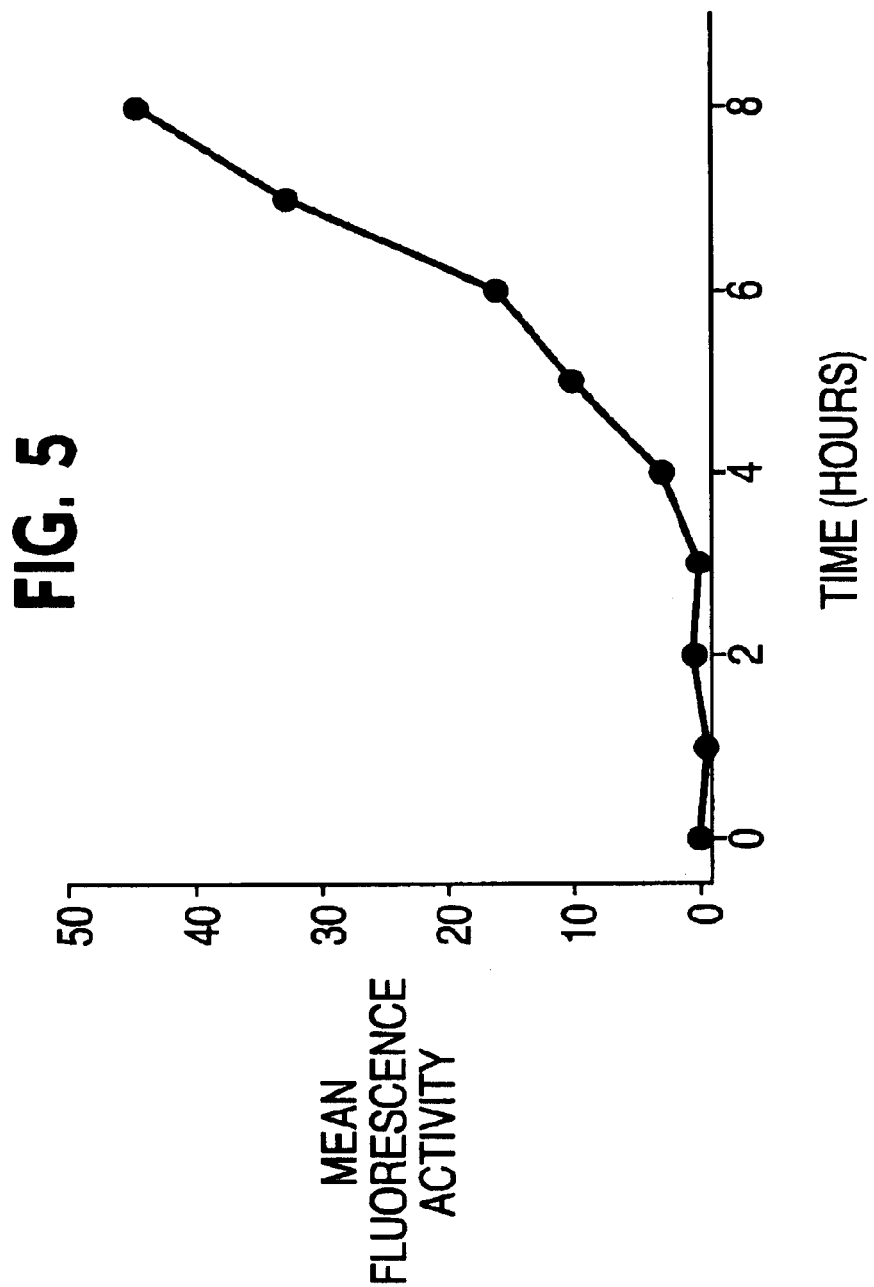
FIG. 5 is a graph showing scFv penetration through pig corneal stroma (epithelial barrier removed) at pH 7.0.

ScFv penetration through the corneal stroma was tested in a first set of experiments using the corneal perfusion chamber. The corneal epithelium was removed prior to the experiment. As shown in FIG. 5, the scFv penetrated successfully through the stroma of pig corneas and retained its specific antigen binding activity. There was a four-hour interval between the first drop of scFv on the donor side and the detection of a clear binding activity on the recipient chamber side.

Figure 6:
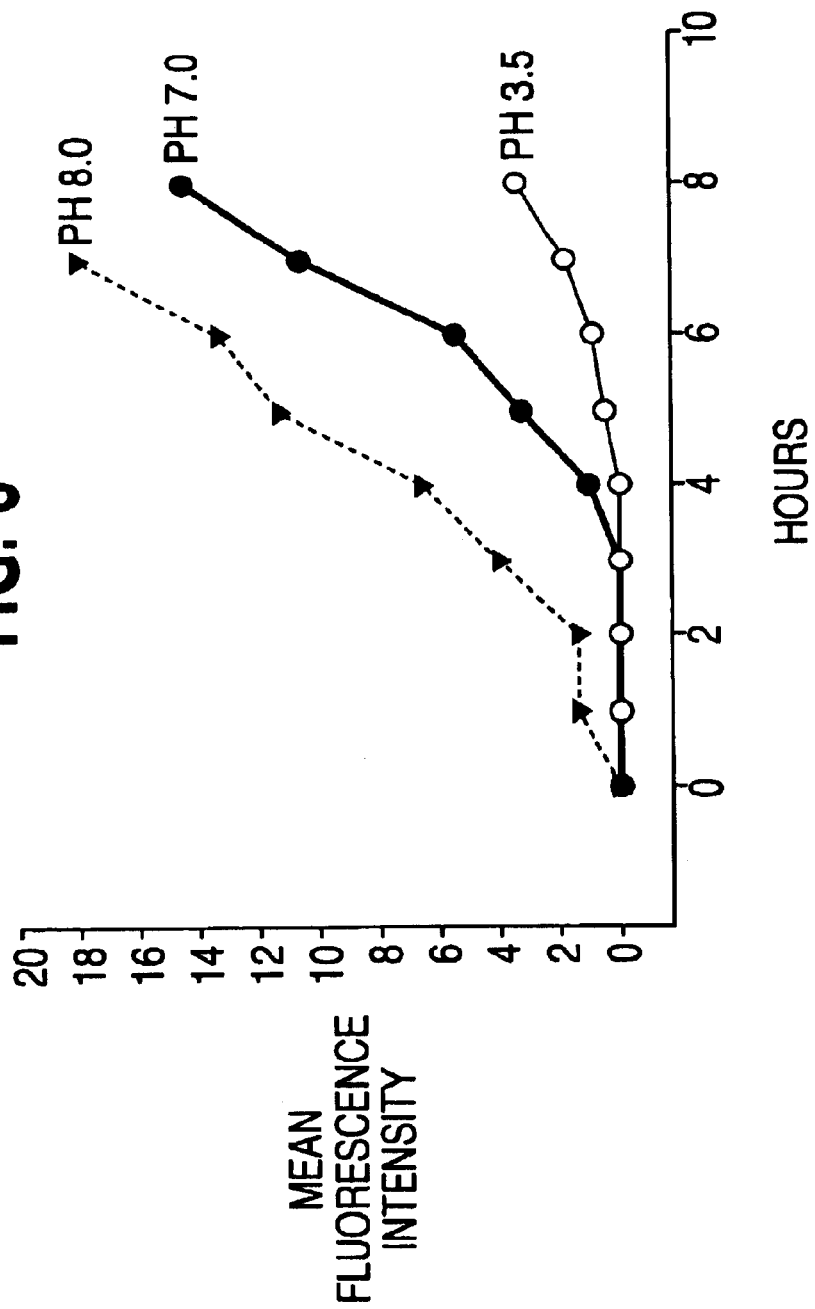
FIG. 6 is a graph showing scFv penetration through pig corneal stroma (epithelial barrier removed) at pH 8.0, pH 7.0 and pH 3.5. Lowering the pH from 7.0 to 3.5 has an adverse effect on penetration. In a cornea with intact epithelium, no penetration could be detected with scFv at a pH of 3.5.

The pH of the buffer in which a drug is dissolved can often influence drug solubility and corneal penetration. The OX38 scFv has an isoelectric point of 6.1, at which pH the scFv penetration is expected to be worst. We therefore investigated penetration of the OX38 scFv fragment through pig corneal stroma at pH of 8.0, 7.0 and 3.5. While an increase in pH from 7.0 to 8.0 resulted in an accelerated penetration, lowering the pH away from the isoelectric point to 3.5 caused a reduction in penetration (FIG. 6).

Figure 7:
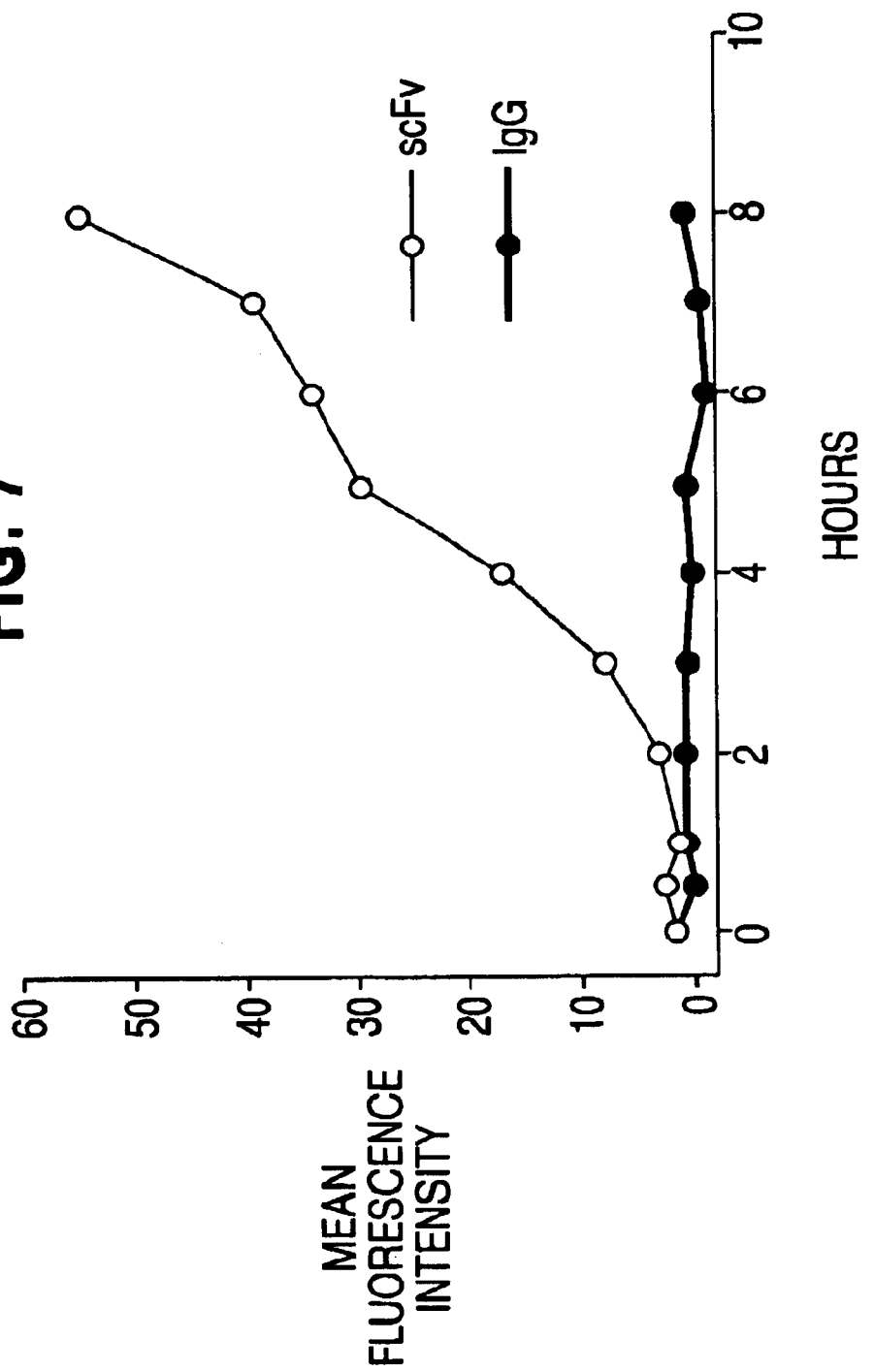
FIG. 7 is a graph showing that in cat corneas without epithelial barriers pure scFv penetrated rapidly with increasing binding activity on the donor side after 3 hours. Feline corneas are 20–40% thinner than porcine corneas explaining the faster penetration. Whole antibodies (mAb) did not penetrate within an observation period of 8 hours.

To prove species-independent stromal penetration, the experiment was repeated with a normal cat cornea. Results from the perfusion chamber showed a similar penetration of scFv in cats as in pigs. ScFv binding activity after penetration through the 25% thinner cat cornea became detectable after 2 hours (FIG. 7).

Figure 10:
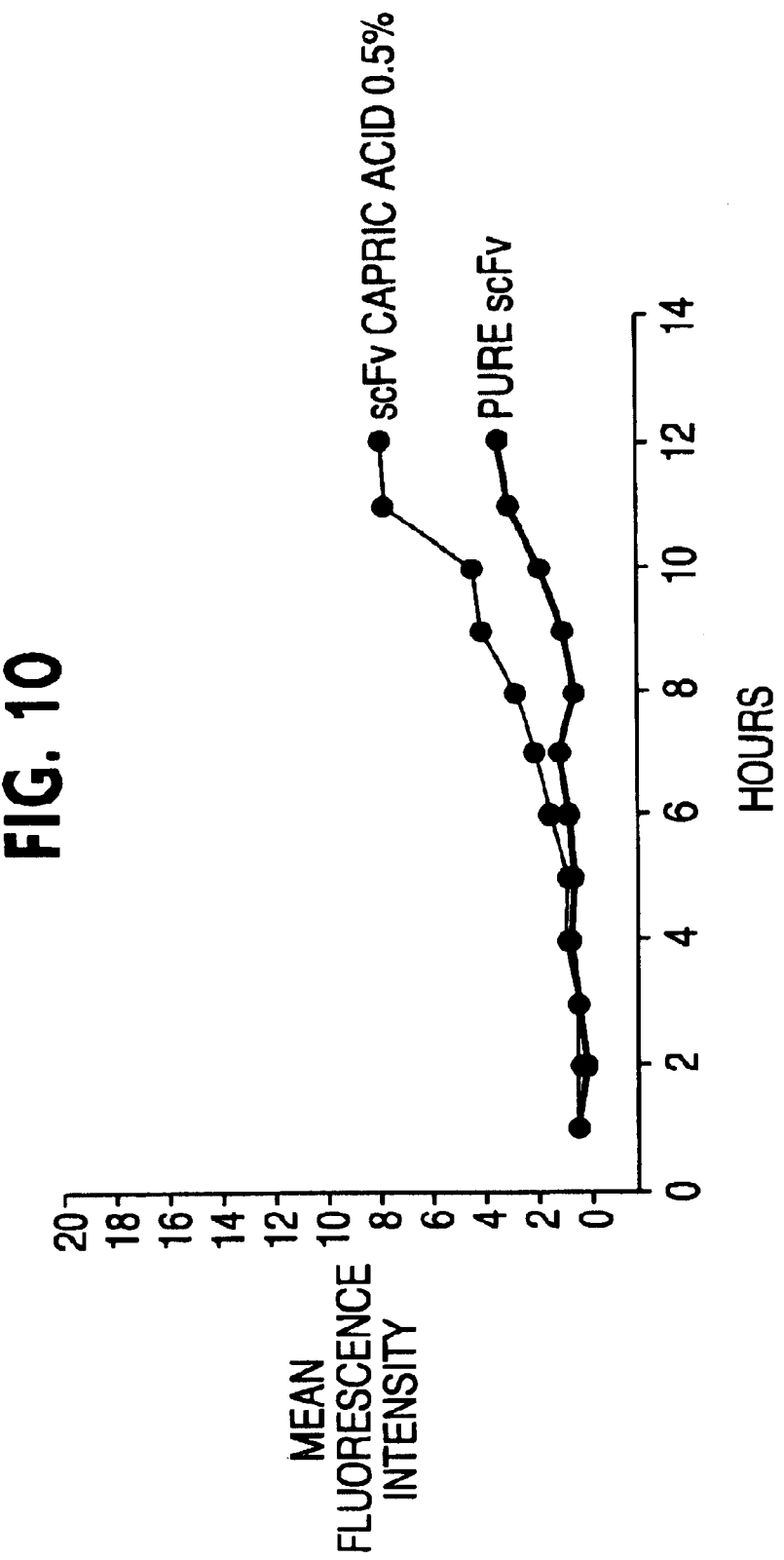
FIG. 10 is a graph showing OX38 scFv penetration through intact pig corneas in perfusion chambers in the presence and absence of 0.5% capric acid.

To prove that these positive penetration results were not caused by tissue damage at the clamped edges of the cornea or by a leakage around the mounted cornea that could have simulated stromal penetration, whole OX38 IgG antibodies were used as a negative control. Whole antibodies are not expected to penetrate the stroma because of their molecular size of about 150 kDa. This clearly exceeds the molecular cut off range of 60–90 kDa for stromal penetration. Monoclonal antibodies at a concentration that allowed positive detection at a dilution of 1 part in 2 million were administered as eye drops every 20 minutes. No binding activity was found on the recipient side during sampling periods of up to 14 hours (FIGS. 6 and 10).

Figure 8:
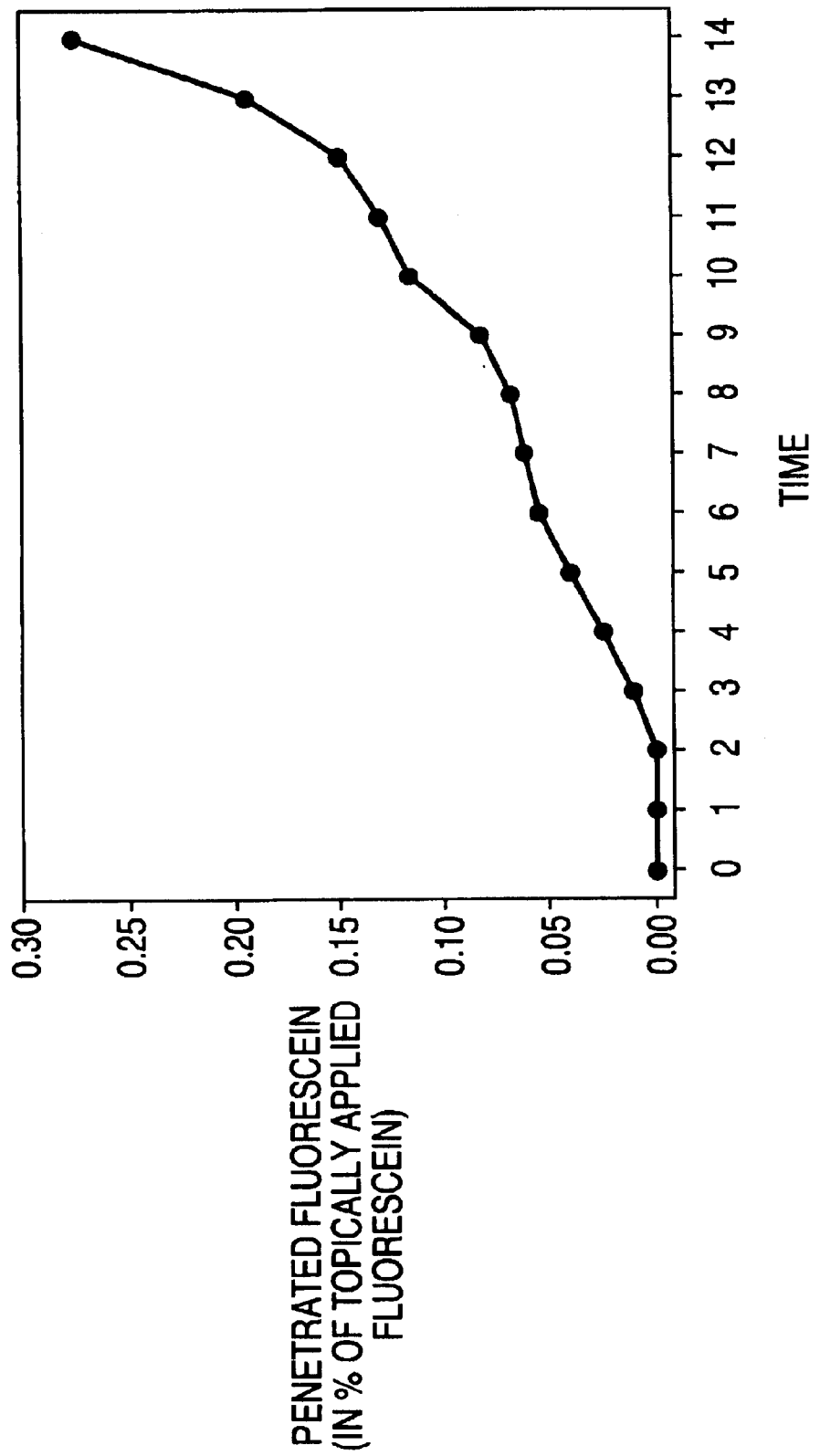
FIG. 8 is a graph showing sodium fluorescein penetration through an intact pig cornea in the perfusion chamber. On the recipient side of the pig cornea, sodium fluorescein became detectable only after 3 hours with a subsequent exponential increase during the rest of the experiment

Penetration experiments in the perfusion chambers allow individual corneas to be studied over an extended period of time, with repetitive sampling of the recipient side to assess the kinetics of the penetration process. However, as the fragments that have penetrated across the cornea into the perfusion chambers become diluted in a large volume (4 mL), the results underestimate the concentration of scFv and miniantibodies that are achievable in a real eye with an anterior chamber volume of 0.3–0.5 mL. To allow a rough comparison of the penetration results obtained in the perfusion chamber experiments with the expected values in an eye of a living human being, additional penetration experiments in the perfusion chambers were carried out using sodium fluorescein eye drops. Sodium fluorescein is a 332 Da molecule, the penetration of which into the human eye has been studied extensively in vivo. After a single drop of 2% (w/v) fluorescein, the drug becomes detectable in the human eye after 30 minutes (Araie et al, 1983, *Jpn J Ophthalmol* 27(3): 421–33). Repeating the administration of fluorescein causes a further substantial increase in the amount to be found in the anterior chamber (Adler et al, 1971, *Exp Eye Res* 11(1): 34–42). To be able to compare the scFv penetration results obtained in pig eyes, a pig cornea with normal epithelium was treated with fluorescein 2% eye drops every 20 minutes for 14 hours. One hundred-microlitre samples were removed from the chamber reservoir in the same manner as for the scFv and miniantibody experiments. Sodium fluorescein concentration was determined in an ELISA reader at 492 nm with a detection threshold of 2 parts per million. On the recipient side of the pig cornea, sodium fluorescein became detectable only after 3 hours with a subsequent exponential increase during the rest of the experiment as shown in FIG. 8.

To allow a better estimation of the scFv concentration that is achievable in a normal eye, scFv penetration was also tested in the whole eye model. In this model each eye can be sampled only once, requiring many eyes with different exposure times to give some kinetic information. However, as the anterior segment of the eye is, in a physiological sense, a well defined structure with only minimal pharmacological interaction with the rest of the body, results from such whole eye experiments reflect more closely the amount of penetration that is achievable in vivo.

Figure 9:
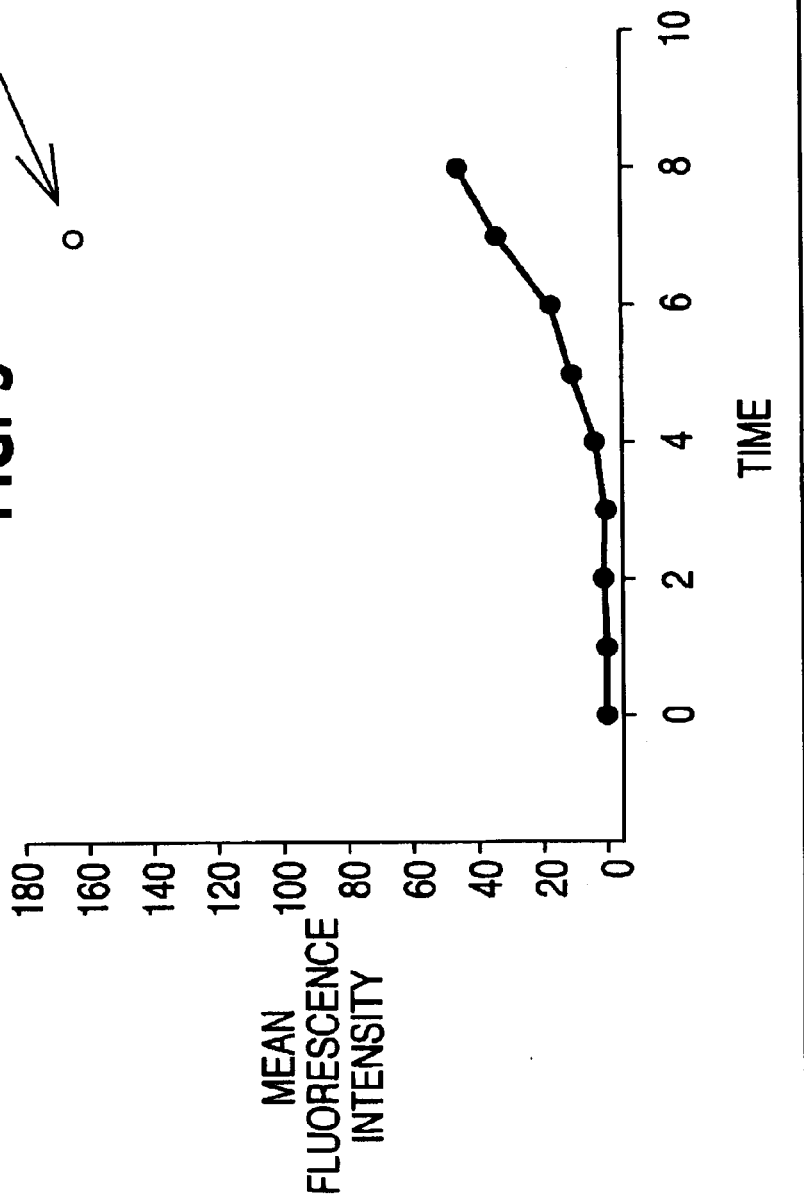
FIG. 9 is a graph showing the relationship between penetration of scFv in corneal perfusion and whole globe penetration experiments. The arrow indicates scFv-binding activity in the anterior chamber of the whole eye (without epithelium).

For this experiment, the corneal epithelium of a whole pig eye was removed and the cornea immersed in OX38 scFv-containing Teflon well for 7 hours. After thoroughly cleaning the surface, a 100-µL sample of anterior chamber fluid was obtained through a syringe with a 27G needle. The binding activity was tested in a FACS assay on rat thymocytes with a detection threshold of 1 part per two thousand. The anterior chamber fluid that was sampled after 7 hours revealed a strong binding activity that was equivalent to a scFv concentration of 1 part in 250 (FIG. 9).

The kinetics of scFv penetration through the corneal epithelium was studied more closely in the perfusion chambers using intact corneas. There was no detectable binding activity over a penetration period of 8 hours when scFv in pure PBS solution (pH 7.2–7.4) were applied as an eye drop. When the scFv/PBS solution was supplemented with 0.01% benzalkonium chloride, a commonly used preservative for eye drops, weak binding activity was observed at the end of the eight hour sampling period in pig corneas (data not shown).

The same experiment was repeated with scFv in PBS at a pH of 8.0 (adjusted with 1M NaOH). Under these conditions scFv penetrated even without a penetration enhancer through a healthy epithelium and stroma, showing increasing binding activity on the recipient side after 8 hours. The addition of 0.5% capric acid resulted in a facilitated corneal penetration with increasing binding activity detectable after 6 hours (FIG. 10).

Corneal Penetration of OX38 Miniantibodies (66.8 kDa)

Figure 11:
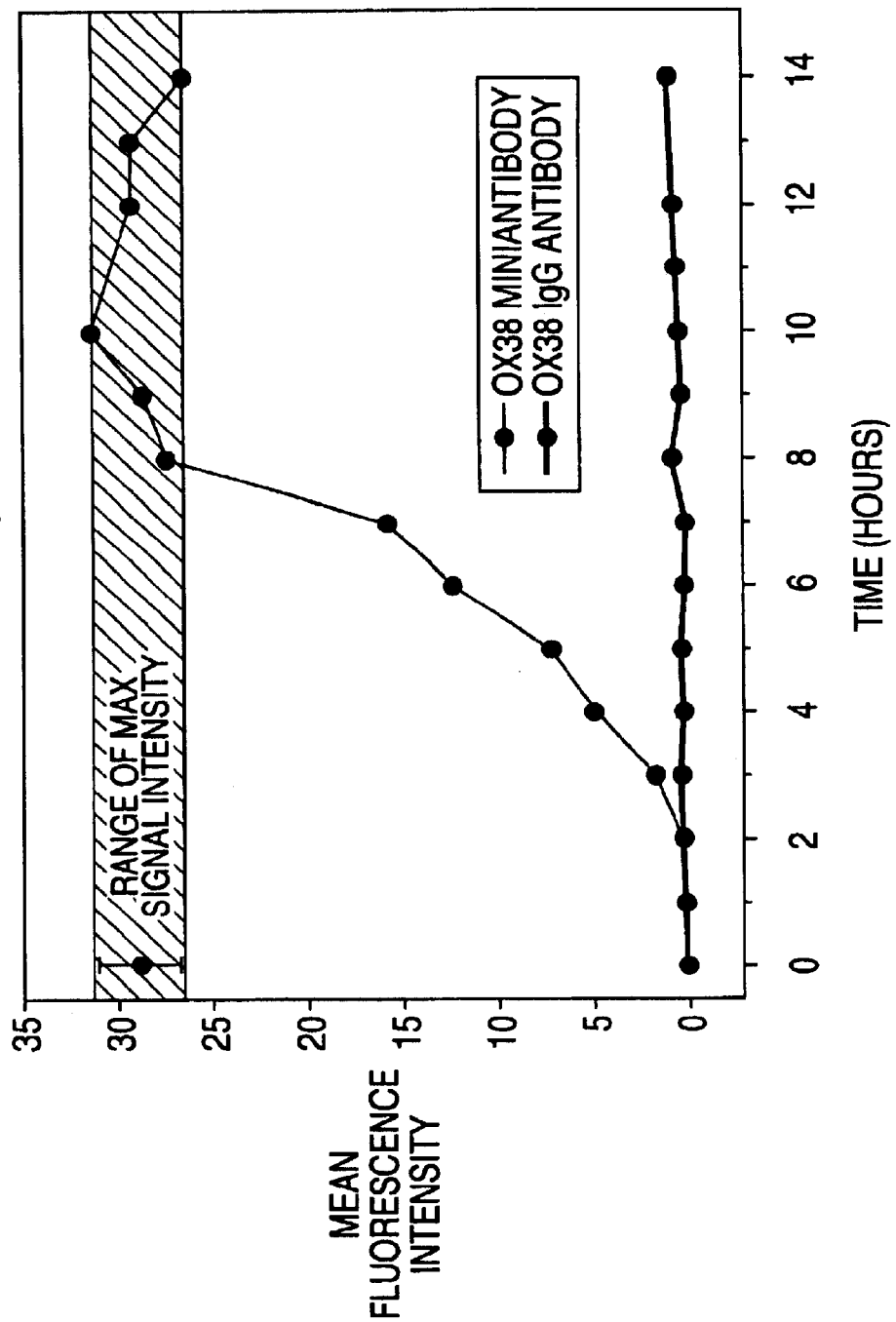
FIG. 11 is a graph showing penetration of miniantibodies and whole IgG-antibodies through pig corneal stroma in the perfusion chamber.

The penetration of OX38 miniantibodies with a molecular size of 66.8 kDa through the corneal stroma was tested in an identical way as that of the monovalent scFv fragments in the perfusion chamber. No penetration of whole OX38 IgG antibody, used as a negative control, could be detected during the whole experimental period of 14 hours. In contrast, OX38 miniantibody binding became positive after 3 hours with a further exponential increase until the fluocytometer assay reached saturation with the 8-hour and subsequent samples (FIG. 11).

Penetration of OX38 miniantibody without penetration enhancer through a pig cornea with an intact epithelial barrier was much slower and became weakly detectable only after 11 hours.

Figure 12:
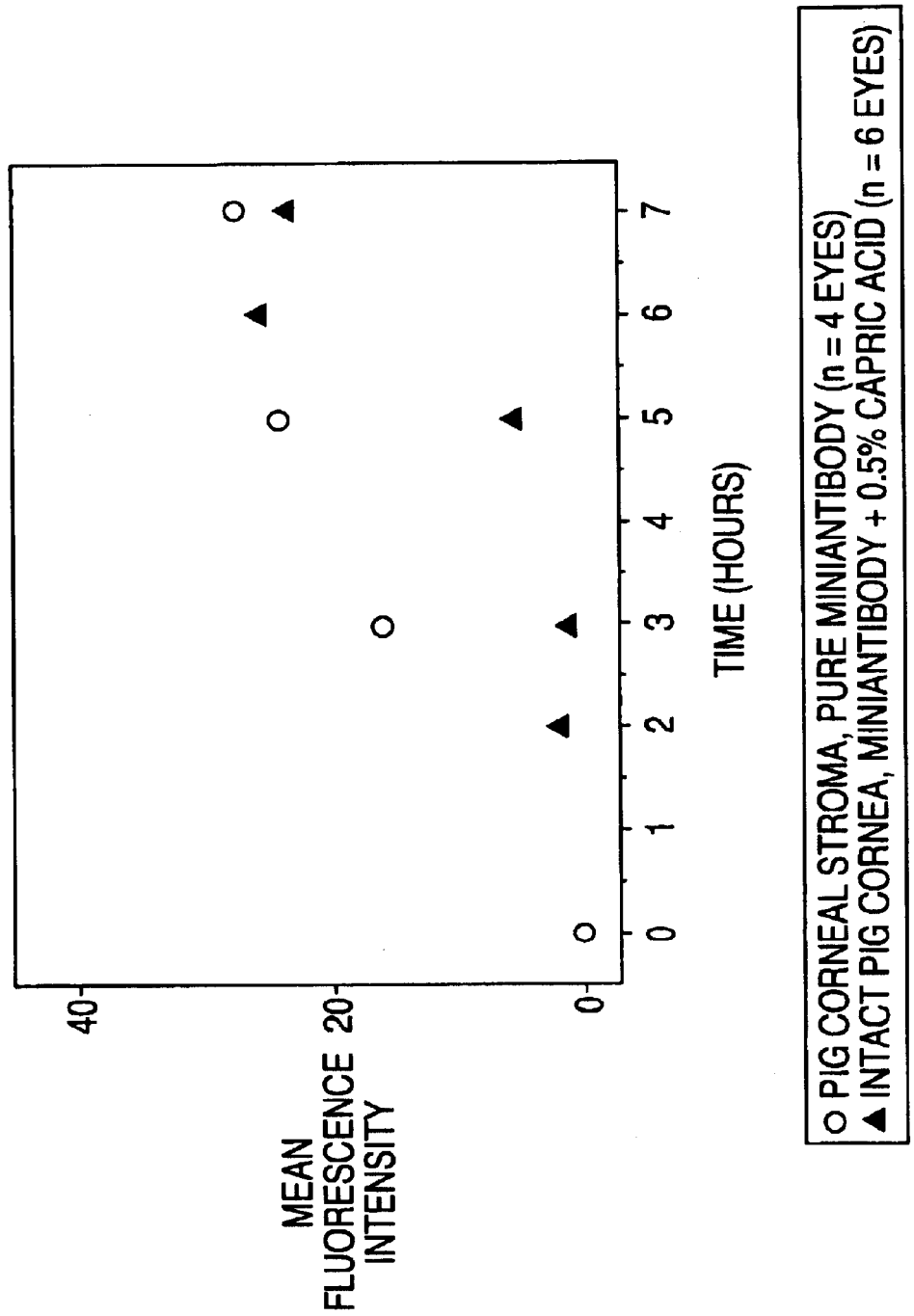
FIG. 12 is a graph showing penetration of miniantibodies through corneal stroma and intact corneas in whole pig eyes.

As with the monovalent scFv, the achievable concentration of miniantibodies in the anterior chamber of a normal eye was investigated in the whole eye model. Pig eyes with the corneal epithelium removed were first sampled after 3 hours and revealed already half the maximal signal intensity. Samples after 5 and 7 hours of miniantibody exposure showed binding activity within the range of a maximal test signal. Subsequently six pig eyes with normal epithelial barrier were exposed to miniantibodies supplemented with 0.5% capric acid. Miniantibody binding activity became clearly detectable in eyes sampled after 5 hours exposure time and activity after 7 and 8 hours was only minimally lower than in eyes without an epithelial barrier (FIG. 12).

Figure 13:
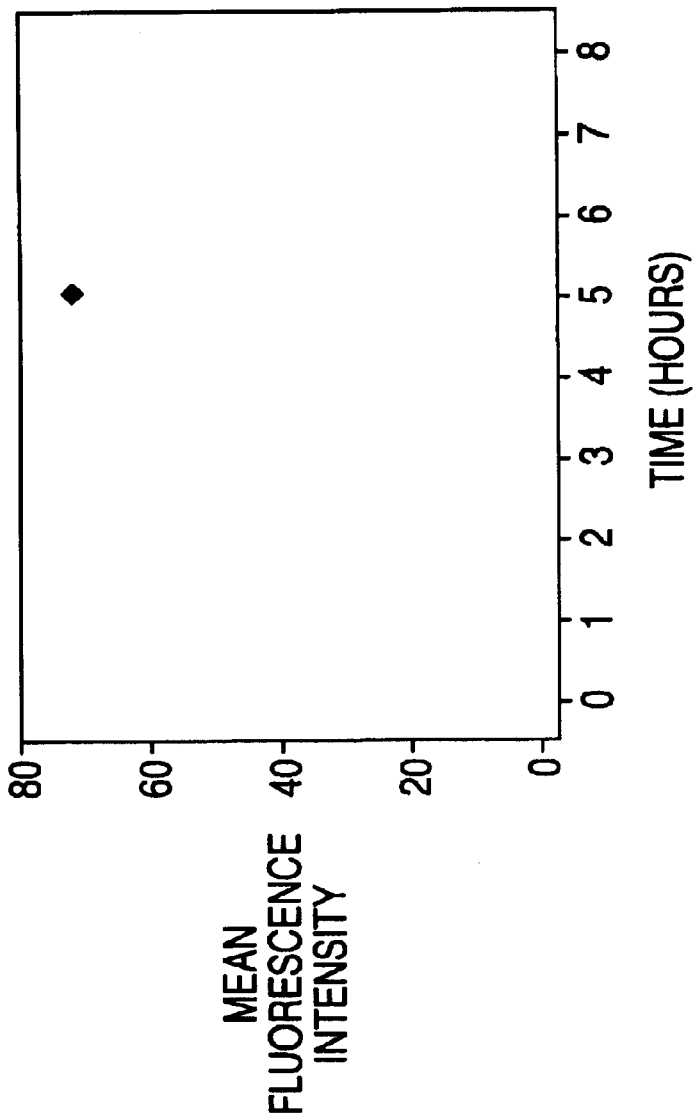
FIG. 13 is a graph showing penetration of OX38 miniantibodies through an intact human cornea in the whole eye penetration set-up.

The most challenging conditions in all the experiments above were the penetration of the relatively large miniantibodies through corneas with an intact epithelial barrier. All these results were obtained in young pig eyes that have a 25% thicker stroma than a human cornea. However, the most important penetration barrier is the epithelial surface and the knowledge of the ultrastructure of this barrier in pig eyes is limited. To compare the above penetration results obtained in pig and cat eyes with potential penetration of sub-immunoglobulin fragments through a human cornea, the most challenging experimental conditions were used in a fresh human eye. This eye with an intact epithelium was treated with OX38 miniantibody in the whole eye set-up. The cornea was exposed for five hours to 100 µL of the standard miniantibody concentration of 1.8 mg/mL supplemented with 0.5% capric acid at pH 8.0. The intraocular sample obtained after 5 hours revealed maximal signal intensity in the fluocytometer, completely saturating $1.5 \times 10^6$ thymocytes per mL. A titration of binding activity in this sample revealed a miniantibody concentration of 0.8 µg/mL in the anterior chamber of this human eye examined (FIGS. 13 and 14).

Discussion

This study demonstrates that engineered recombinant antibody fragments can successfully penetrate the cornea to reach inside the eye after topical administration as eye drops. Moreover these fragments retain their full antigen binding activity, offering the possibility of an antibody based therapeutic and diagnostic intervention in the eye. At the same time this study has, as many others before (Verhagen et al, 1990, *Invest Ophthalmol Vis Sci* 31(8): 1519–25; Osusky et al, 1993, *Graefes Arch Clin Exp Ophthalmol* 231(2): 122–8), shown that naturally-occurring whole antibodies do not, or a least not in a therapeutically useful manner, penetrate the cornea and that the cut-off for the maximal molecular size that enables penetration through the cornea is much lower than the 500 kDa found in a frequently cited but never repeated study (Maurice D, Mishima S. *Ocular Pharmacokinetics*. Springer-Verlag Berlin. 1984. Sears M, ed. Pharmacology of the Eye).

The cornea contains two important penetration barriers, the superficial corneal epithelium and the corneal stroma. The corneal epithelium forms a strong penetration barrier for all but small lipophilic molecules. Larger molecules have to penetrate through the intercellular space that is normally blocked by tight junctions (Maurice D M., 1980, *Int Ophthalmol Clin* 20(3): 7–20; Burstein et al, 1985, *J Ocul Pharmacol* 1(3): 309–26). Pores within these tight junctions allow penetration of molecules up to a size of 1–5 kDa (Edelhauser et al, 1998, *Adv Exp Med Biol* 438: 265–71). The corneal epithelial penetration barrier depends on healthy cellular structures. It is well known that the epithelial barrier function in humans is significantly reduced by ageing (Chang et al, 1993 *Cornea* 12(6): 493–9 [see comments]) and many common diseases such as diabetes or dry eyes (Gobbels et al, 1989, *Graefes Arch Clin Exp Ophthalmol* 227(2): 142–4; Yokoi et al, 1998, *Br J Ophthalmol* 82(7): 797–800). In addition to that, several studies have shown that surgical interventions such as corneal transplantation (Shimazaki et al, 1999, *Cornea* 18(5): 559–64; Chang et al, 1994, *Ophthalmic Res* 26(5): 283–9) or trabeculectomies (Tanihara et al, 1997, *Am J Ophthalmol* 123(4): 487–93) to treat glaucoma result in a breakdown of the barrier function for months or even years.

The second barrier, the corneal stroma, allows penetration of larger fragments and has been cited to allow penetration of molecules up to 500 kDa or even larger molecules if the tissue becomes oedematous (Burstein et al, 1985, supra). However the figure of 500 kDa is derived from a single study that was published in the non-peer reviewed literature (Maurice et al, 1984, supra). In fact, several studies have addressed the penetration of IgG antibodies with a size of 150 kDa. These studies have repeatedly shown that molecules of this size do not penetrate the cornea, or penetrate only at an exceedingly slow rate requiring a time interval of 1–2 weeks to cross the corneal stroma (Verhagen et al, 1990, supra; Osusky et al, 1993, supra). In contrast to the epithelial barrier there are no known penetration enhancers to improve drug delivery though the corneal stroma.

The data presented above demonstrate that recombinant antibody fragments at least up to a size of 66 kDa can rapidly penetrate the corneal stroma and retain their full antigen-binding capacity inside the eye. Penetration of these antibody fragments seems to be species independent as penetration could be documented in pigs, cats and humans. Stromal drug penetration has an indirect linear correlation to stromal thickness and drug size and a direct correlation to drug concentration (Burstein et al, 1985, supra). The faster penetration of scFv through the 25% thinner cat and human cornea than through the pig cornea seems to be in good agreement with the finding above. The fact that the two and a half-fold larger miniantibody was detected on the recipient side of the corneal perfusion chamber after a similar time interval as the small scFv fragment is probably due to the 7–8 fold higher concentration of miniantibodies in the eye drops used in this study. An increase of the scFv concentration as we have demonstrated with the two step purification process for clinical grade material is therefore likely to result in even higher intraocular concentrations than the ones found in the present study.

As mentioned above, the superficial epithelium is the stronger barrier against drug penetration and it is therefore no surprise that the penetration of scFv and miniantibody fragments through corneas with an intact epithelial barrier is considerably slower. In fact it is rather surprising that scFv and miniantibodies could be shown to penetrate, albeit at a very low rate, through an intact epithelial barrier at all. However, the epithelial barrier interferes even with much smaller molecules to an extent that most of the currently used ophthalmic drugs are supplemented with some form of penetration enhancer. These penetration enhancers work by loosening the tight junctions of the most superior epithelial cells (Burstein N L. 1985, *Trans Ophthalmol Soc U K* 104(Pt 4): 402–9; Ashton et al, 1991, *J Pharmacol Exp Ther* 259(2): 719–24; Green et al, 1971, *Am J Ophthalmol* 72(5): 897–905). The most commonly used penetration enhancer is benzalkonium chloride (Tang et at, 1994, *J Pharm Sci* 83(1): 85–90; Burstein N L. et al, 1980, *Invest Ophthalmol Vis Sci* 19(3): 308–13), which also works as preservative against microbial contamination. It is usually added to a final concentration of 0.01–0.05%. A future pharmaceutical preparation of recombinant antibody fragments in the form of eye drops will need preservatives independently of their epithelial penetration properties. We therefore supplemented some of the scFv and the miniantibody fragments in this study with 0.5% capric acid, a normal dairy food constituent that results in a reversible increase in tight junction permeability in the intestinal mucosa as well as in the corneal epithelium (Morimoto et al, 1989, *Arch Int Pharmacodyn Ther* 302: 18–26; Soderholm et al, 1998, *Dig Dis Sci* 43(7): 1547–52; Sasaki et al, 1995, *Pharm Res* 12(8): 1146–50). Capric acid improved scFv and miniantibody penetration through an intact epithelium considerably. In contrast to other penetration enhancers such as benzalkonium chloride, digitonin or Tween20, corneas treated with 0.5% capric acid showed no epithelial alterations when examined with conventional histology.

The single human eye that could be obtained for these penetration experiments received miniantibodies supplemented with 0.5% capric acid. The miniantibody binding activity found in the human anterior chamber fluid after 5 hours greatly exceeded the penetration found in pig eyes after the same time. This could reflect a primarily lower penetration barrier of this 77-year old human cornea in comparison to the 8–14 months old pig eyes or a generally better effect of capric acid in human corneas. However, this remains a speculation until more human eyes can be studied.

In summary this study shows that scFv antibody fragments can penetrate into the eye when given as eye drops. This makes them a potential candidate for a novel class of drugs for the treatment of many ophthalmic diseases, especially prevention and treatment of corneal transplant rejection, inflammatory or infectious keratitis, conjunctivitis and uveitis, as described hereinafter. As scFv can be labelled with different tags they are also considered to have diagnostic potential.

EXAMPLE 2

Experimental Animal Models

Animals

Male and female Fischer 344, DA, Lewis and Wistar-Furth inbred rats and Porton outbred rats aged 6–16 weeks are bred within the Flinders University of South Australia (Adelaide, Australia). Rats are housed at 21° C. and 50% humidity in a 12-hour light and 12-hour dark cycle, and are fed water and dried ration (New Joint Stock, Ridley Agriproducts, Murray Bridge, SA, Australia) ad libitum.

Adult male and female BALB/c or OLA mice are housed at 21° C. and 50% humidity in a 12-hour light and 12-hour dark cycle, and fed water and dried ration (New Joint Stock, Ridley Agriproducts, Murray Bridge, Australia). All procedures and euthanasia are carried out under inhalation general anaesthesia (halothane; Zeneca Ltd, Macclesfield, United Kingdom). Experimental protocols were developed in accordance with the National Health and Medical Research Council of Australia "Guidelines for the Use of Animals in Research", and are always submitted to the Animal Welfare Committee at Flinders University of South Australia for approval.

Induction of Endotoxin-induced Uveitis (EIU)

Rats are injected in one hind footpad with 200 microgram of *E. coli* 055:B55 lipopolysaccharide (Sigma Chemical Company) solubilised in 100 microgram normal saline, according to the method of Rosenbaum et al (1980, *Nature* 286: 611–613). Inflammation becomes apparent at 12 hours post-injection, is maximal at 24 hours and is resolving by 48 hours. Animals are examined and scored at the slit-lamp at 24 hours. We have extensive experience with this model (Smith et al, 1998, *Invest Ophthalmol Vis Sci* 39: 658–661; Immunol Cell Biol 76: 497–512).

Induction of Experimental Melanin-induced Uveitis (EMIU)

Experimental melanin-induced uveitis (EMIU) is a robust and relevant model of acute anterior uveitis (Smith et al., 1998, *Immunol. Cell. Biol.* 76: 497–512; Smith et al., 1999, *Clin. Exp. Immunol.* 115: 64–71). Ocular melanin is extracted from bovine choroids according to the protocol described by Broekhuyse and colleagues (1984, *Curr Eye Res* 3: 1405–1412), and quantified as a dry weight. EMIU is induced in Fischer 344 rats by immunization with 250 $\mu$g purified bovine choroidal melanin emulsified in Hunter's adjuvant, with pertussis toxin co-adjuvant (Broekhuyse and colleagues, 1984, supra; 1995, *Ocul Immunol Inflamm* 3: 149–155; 1996, *Jpn J Ophthalmol* 40: 459–468). Specifically, rats receive 125 microgram of bovine ocular melanin in a 1:1 emulsion of sterile, non-pyrogenic 0.9% normal saline and Hunter's TitreMax™ adjuvant (Sigma Chemical Company, St. Louis, Mo., USA) in a total volume of 60 microlitre by right hind footpad injection. Immediately afterwards, they are injected intraperitoneally with the same quantity of melanin mixed with 1 microgram of pertussis toxin (Sigma Chemical Company) in a total volume of 40 microlitre normal saline. Uveitis is generally bilateral, is apparent 10–20 days after injection, resolves after 2–3 weeks and is recurrent in 20% of animals.

Monitoring of Uveitis and Collection of Uveitic Eyes

Animals are examined daily at the slit-lamp to identify the onset and course of uveitis. Severity is recorded according to a well-validated system in which aqueous cells and flare, presence of fibrin, synechiae, pupil reactivity, iris hyperaemia and empyema are all scored. The scale used is as follows: no inflammation: normal appearance; mild disease: no swelling, but obvious infiltration of anterior uvea, ±cellular exudate in anterior or posterior chambers; moderate disease: mild or moderate swelling and infiltration of anterior uvea, moderate cellular exudate in anterior and posterior chambers; severe disease: massive swelling and infiltration of anterior uvea, large cellular exudate in anterior and posterior chambers with vitritis. Animals are killed by overdose of anaesthetic halothane and the eyes are immediately removed for further processing.

Rat Model of Corneal Transplantation

The present inventors were the first to develop the widely used model of orthotopic corneal transplantation of the inbred rat (Williams & Coster, 1985, *Invest Ophthalmol Vis Sci* 26: 23–30; Williams et al, Corneal transplantation in small animals. In: *Experimental Transplantation Models in Small Animals,* eds. M K Green, T E Mandel. Chur, Switzerland: Harwood Academic Publishers, 1995, chapter 5, pp107–132). Inbred Fischer 344 (F344; major histocompatibility complex (MHC) haplotype $RT^{1vl}$) and inbred Wistar-Furth (WF; MHC haplotype $RT^u$) rats are used for corneal transplantation. Adult F344 rats are the recipients of corneal grafts from either adult F344 rats (isografts) or adult WF rats (allografts). Grafts are not performed across a gender difference, but allografts are performed across MHC class I and II and minor antigen barriers.

A unilateral right penetrating 3-mm diameter corneal graft is performed under general anaesthetic as previously described. Chloramphenicol ointment 1% is applied to the graft post-operatively, but no immunosuppression other than as specified in a particular experiment is administered. Graft sutures are not removed. Recipients are examined daily at the slit-lamp for corneal clarity, anterior segment inflammation, synechiae, and corneal neovascularisation. Specifically, clarity and oedema are each scored on a scale of 0–4, with 0 being completely transparent (for clarity) or thin (for oedema), and 4 being completely opaque (for clarity) or maximally thick (for oedema). Any rat that develops post-operative cataract at any stage or that has corneal opacities on the fifth post-operative day is deemed a technical failure and is excluded from analysis.

Rejection appears as increasing corneal opacity in a previously thin, clear corneal graft and is always associated with graft neovascularisation. The day of rejection is defined as the first day that the pupil margin is no longer clearly visible through the grafted cornea. In the inbred strain combination WF to F344, rejection occurs at a median of 16 days post-graft. Rats that reach 100 days with clear grafts are considered long-survivors.

Mouse Models of HSV Stromal Keratitis

BALB/c mouse corneas are scarified with a needle and 4 $\mu$L containing $10^6$ pfu HSV-1 (clinical isolate) is applied topically (Thomas et al, 1998, *J Immunol* 160: 3965–70). Disease progresses to stromal keratitis over a three-week period. A clinical scoring system is used to follow disease at the slit-lamp: 0—clear cornea, 1—mild haze, 2—moderate opacity or scarring, 3—severe opacification but iris margin visible, 4—iris not visible, 5—necrotising stromal keratitis. A well-characterised model of recurrent HSV keratitis in the NIH/OLA mouse (Harland) is also used (Laycock et al, 1991, *Invest Ophthalmol Vis Sci* 32: 2741–2746). One cornea is scarified and inoculated as above. At the same time, 0.5 mL of pooled human serum containing antibody to HSV (Chemicon, Temecula, Calif.) is given intraperitoneally to protect the eye from damage during the acute phase of infection. The mice are then left for 5 weeks to establish latency. Viral reactivation is achieved using a UVB transilluminator (FS40 Westinghouse lamps). Anaesthetised mice are screened so that only the eye is irradiated. A dose of 248 mJ/cm$^2$ over 55 seconds is optimal for HSV reactivation.

Rat Model of Acanthamoeba Keratitis

Acanthamoeba keratitis is induced by inoculation of the outbred rat cornea with acanthamoebae and a Corynebacterium sp., according to a model developed in our laboratory (Badenoch et al, 1990, *Arch Ophthalmol* 108: 107–112). Adult female Porton rats are anaesthetized. A 2-mm partial-thickness incision is made with a scalpel blade in the peripheral cornea, approximately 1 mm from the limbus. Under the operating microscope, a 1 $\mu$L volume $10^4$ *Acanthamoeba castellanii* (>90% trophoxoites; >90% viability) mixed with $10^6$ *Corynebacterium xerosis* is inoculated using a microsyringe fitted with a 31-gauge needle. The needle is inserted through the wound into the central corneal lamellae. All animals are observed daily after inoculation. Acanthamoeba keratitis develops in all animals, with leucocytic infiltration visible on day 5 and suppurative keratitis well established by day 7.

Statistical Analyses

Experimental groups contain 10 animals. Graft survival and disease incidence data are analysed with the Mann-Whitney U-test corrected for ties. Categorical data (e.g. disease severity scores) are analysed using the two-way Fisher's exact test.

Corneal Photography, Immunocytochemistry, Histopathology and Flow Cytometry

Corneal photography is performed on anaesthetized animals using a Wild Heerbrugg Photoautomat MPS 45 camera attached to the operating microscope (for rats, mice). Immunohistochemistry is performed using an immunoperoxidase technique on cryostat-cut sections of PLP-fixed tissue; a wide range of monoclonal antibodies directed against rat and mouse leucocyte and other cell surface markers that will allow precise identification of the composition of corneal leucocytic infiltrates. Histopathological correlations are made on H&E sections of formalin-fixed, paraffin-embedded whole eyes. Flow cytometry is performed using a standard single-colour indirect immunofluoresence and a high-sensitivity technique.

Additional Antibodies Used in Antibody Engineering

Anti-rat B7-1 (CD80: 3H5; IgG1) and anti-B7-2 (CD86: 24F; IgG1) hybridomas were the kind gift of Dr H Yagita (Juntendo University, Tokyo, Japan). The anti-CD28 hybridoma (JJ319; IgG1) was the generous gift of Dr T Hunig (Institute for Virology and Immunology, University of Wurzburg, Germany). Anti-poly-histidine antibodies (HIS-1; mouse; IgG2a) was purchased from Sigma Chemical Company (St Louis, Mo., USA). FITC-conjugated goat anti-mouse immunoglobulins were purchased from Silenus Laboratories (Melbourne, VIC). Horseradish peroxidase-conjugated streptavidin and biotinylated goat anti-mouse immunoglobulins were purchased from DAKO Corporation (Carpinteria, Calif., USA).

Administration of Antibody Reagents

Systemic administration can be performed by intraperitoneal (ip) injection of antibody in buffered saline with 1% foetal calf serum (FCS) added as a carrier. The regimen of injection depends upon the experiment. Topical administration can be performed by directly application to the cornea of antibody in ophthalmic Balanced Salt Solution and supplemented with 1% FCS and one or more penetration enhancers.

Ascites Production

To generate monoclonal antibody as ascites, hybridoma cells are injected intraperitoneally into separate groups of pristane-treated BALB/c mice according to standard methods. Ascites is collected aseptically after the mice have been euthanased. The resultant ascites is diluted with sterile, pyrogen-free PBS containing 1% v/v foetal calf serum.

Monoclonal Antibodies Used for Immunohistochemistry

Mouse monoclonal antibodies used in the immunohistochemical identification of rat or mouse cell surface antigens are produced as undiluted supernatants from stationary phase hybridomas. Hybridomas X63 (unknown specificity; IgG1 isotype negative control), OX-1 (anti-CD45 [leucocyte-common antigen]; IgG1 isotype), OX-35 and OX-38 (anti-CD4; IgG1 and IgG2a isotypes, respectively), OX-8 (anti-CD8; IgG1 isotype), NDS61 (anti-CD25 [Interleukin-2 receptor (IL-2R)]; IgG1 isotype), R73 (anti-T cell receptor (TCR); IgG1 isotype), OX-26 (anti-CD71 [transferrin receptor]; IgG2a isotype), OX-42 (anti-CD11b/CD 18 [C3b receptor]; IgG2a isotype), ED-1 (anti-rat monocyte, macrophage and dendritic cell cytoplasmic antigen; IgG1 isotype) and OX-6 (anti-MHC monomorphic class II determinant; IgG1 isotype) were obtained from the European Collection of Animal Cell Cultures, and hybridoma SAL5 (anti-Salmonella antigen; IgG2a isotype negative control) was a gift from Dr. L. Ashman (University of Adelaide, Adelaide, Australia). Hybridomas producing monoclonal antibody to various mouse surface markers (mouse CD4 (GK1.5), CD8 (TIB150), CD11b/c (TIB213, HB8466) and IL-2 receptor (PC61) were the gifts of Dr P Macardle and Dr P H Hart, both of Flinders University.

Immunohistochemical Staining for Cell Surface Antigens

After euthanasia of the rat or mouse, eyes were enucleated and were punctured posterior to the pars plana, pre-fixed by immersion at 4° C. in 2% weight/volume (w/v) paraformaldehyde-0.075 M lysine-0.0375 M sodium phosphate-0.01 M sodium periodate for 4 hours and dehydrated in sequential changes of 7% and 15% w/v sucrose in Dulbecco's A phosphate-buffered saline (PBS), embedded in OCT compound (Miles, Elkhart, Ind., USA) and snap-frozen in liquid nitrogen. Ocular cross-sections were cut by cryostat at 5–8 micron thickness. Sections were incubated for 10 minutes at room temperature with 10% v/v normal swine serum (Commonwealth Serum Laboratories, Melbourne, Australia) in Dulbecco's A phosphate-buffered saline (PBS), then with the primary antibody for 18 hours. At this point and subsequently the sections were washed with PBS containing 0.2% w/v gelatin. They were incubated for 30 minutes with biotinylated affinity-isolated goat anti-mouse immunoglobulin (DAKO Corporation, Carpinteria, Calif., USA) diluted 1 in 500 in PBS containing 1% v/v normal rat serum, washed, and then incubated for a further 30 minutes with horseradish peroxidase-conjugated streptavidin (DAKO Corporation) diluted 1 in 1000 in PBS. Sections were washed and developed for 5 minutes in 9 mM Tris-HCl buffer at pH 7.6 with 40 mM sodium azide, 20 mM 3,3'-diaminobenzidine tetrahydrochloride, 9 mM imidazole, and 0.07% v/v hydrogen peroxide (Sigma Chemical Company). Reactivity and specificity of antibodies were checked by flow cytometry on appropriate rat or mouse target cells (normal cells and/or transfectants) prior to their use in immunohistochemistry, and on fixed sections of non-ocular tissue prior to their use in the eye.

Histological Assessment of Rat and Mouse Eyes

Enucleated eyes are fixed for a minimum of 24 hours in 10% buffered formalin, dehydrated to 100% ethanol, further fixed for 18 hours in chloroform, and embedded in paraffin wax. Tissue cross-sections are cut 5 micron thick and stained with haematoxylin and eosin.

Monitoring of Rat Peripheral T Cell Subsets in vivo

Peripheral T cell subsets were monitored by flow cytometry of tail blood preparations. Samples were collected from rats just prior to the first antibody injection and on days 7, 14 and 28 after disease induction. Up to 1 mL of peripheral blood was collected into a lithium heparin-coated tube, and diluted to 5 mL with HEPES-buffered RPMI 1640 medium (ICN Biomedicals Inc., Aurora, Ohio, USA) containing 100 IU/mL penicillin. 100 microgram/mL streptomycin sulphate, 2 mM glutamine and 10% v/v foetal calf serum. Lymphocytes were separated using Lymphoprep™ (Nycomed Pharma As, Oslo, Norway) as described by the manufacturer, except that 40 mM meglumine diatrizoate (Angiografin, Schering AG, Berlin, Germany) was used to adjust the specific gravity of Lymphoprep to 1.09. The recovered cells were suspended in PBS-0.02 M sodium azide (PBS-azide) at 1×10$^7$ cells/mL, and to 50 microlitre of this lymphocyte suspension was added 50 microlitre of monoclonal antibody. This mixture was incubated on ice for 30 minutes, then washed in PBS-azide and centrifuged at 400×g for 5 minutes at 4° C. The pellet was re-suspended in 25 microlitre of normal rat serum and 50 microlitre of FITC-conjugated goat anti-mouse immunoglobulin (Silenus Laboratories, Melbourne, Australia) diluted 1 in 50 with PBS-azide. A 30-minute incubation on ice was followed by two consecutive washes. The cell pellet was re-suspended in 50 mL of fixative containing 10 mM glucose, 5% v/v formaldehyde and 5 mM sodium azide in PBS. Antibody binding was measured by flow cytometry using a standard fluorescein filter set (FACScan™, Becton Dickinson, Mountain View, Calif., USA).

Endotoxin Assay

Endotoxin levels were measured by the Multi-test Limulus Amebocyte Lysate assay (Whittaker Bioproducts, Walkersville, Mo., USA) (sensitivity=0.125 EU/mL) according to the manufacturer's instructions.

Protein Estimation

Total protein in reagents was measured by a modified Lowry procedure using a commercial protein estimation kit (Sigma Diagnostics, St Louis, Mo., USA) following the manufacturer's instructions. Absorbance was measured at 750 nm.

Rat Mixed Lymphocyte Reaction

Mononuclear cell fractions were isolated by density centrifugation on Lymphoprep (Nycomed Pharma, Oslo, Norway). Twenty-thousand viable responder splenocytes were incubated with 2×10$^5$ mitomycin C-inactivated (250 ng/ml, 37° C. for 30 mins; Kyowa Hakko Kogyo Co Ltd, Kyowa, Japan) stimulators in a final volume of 250 µL whole RPMI media (20% v/v FCS, 100 IU/mL penicillin, 100 µg/mL streptomycin, 2 mM L-glutamine, 5×10$^{-5}$ M 2-mercaptoethanol) in 96-well round-bottomed microtitre plates. Monoclonal antibody reagents or fragments were added and cultures incubated with 5% CO— in humidified air at 37° C. for 6 days. To measure cell proliferation, 1 µCi tritiated thymidine (Amersham, Buckinghamshire, UK) was added to the cultures for the final 18 hours. Following harvesting, the impregnated glass fibre papers were placed into masks and 20 µL scintillation fluid added to each well. Papers were counted in a Topcount™ counter. All cultures were performed in triplicate.

EXAMPLE 3

Evaluation of Engineered Antibody Fragments in vitro

Functional activity of monovalent or divalent antibodies in vitro is compared with the parent whole monoclonal antibody and with irrelevant control scFvs. Fragments may be tested singly and in combination. If the scFvs contain the "tag" sequence poly-His, detection for flow cytometry and immunohistochemistry can be accomplished by use of a monoclonal antibody (HIS-1, Sigma) to the tag. However, it will be understood that other identification tags can similarly be used. To confirm appropriate specificity of the engineered constructs, binding is assessed by flow cytometry on unfixed normal rat cells or transfectants, and/or immunohistochemistry on cytocentrifuge preparations of fixed transfectants, normal rat or mouse cells, mitogen-stimulated rat spleen cells, HSV-infected Hep-2 cells and MRC-5 fibroblasts, or cultured Acanthamoeba cells. Activity is titrated by flow cytometry where appropriate. Tissue binding is assessed on 5–8 µm cryostat-cut sections of PLP-fixed normal rat eye, lymph node, spleen, kidney, heart and liver by immunoperoxidase staining. Flow cytometry on peripheral blood collected from the tail vein is used to determine whether fragments have bound to circulating cells in vivo scFv administration. ScFv affinity on/off rates will be examined with an optical biosensor (BIAcore™) using purified antigen as the solid phase.

EXAMPLE 4

Modulation of EMIU by scfv

We will first test anti-CD4 scFv, as we have already shown that whole anti-CD4 (but not CD8) monoclonal antibody blocks de novo disease development in EMIU and may block recurrent disease (Smith et al., 1999, Clin. Exp. Immunol. 115: 64–71). Anti-ICAM-1 scfv will then be examined. Controls will include groups receiving no treatment other than disease induction, disease induction plus negative control scFv, and disease induction plus whole monoclonal antibody. For systemic administration, rats will be injected ip with >1 mg/mL protein scFv (1 mL volumes) at 3 days prior to disease induction, on the day 0 and on days 3, 5, 7, 9 and 11 thereafter, and incidence and severity of uveitis measured by slit-lamp examination. Experiments to determine the appropriate therapeutic dose will need to be performed: in a preliminary experiment, systemic administration of 1 mg/mL total protein of anti-CD4 scFv prevented EMIU in over 30% animals tested (see Table 1).

TABLE 1

| Antibody | Incidence uveitis |
| --- | --- |
| Controls | 27/28 (96%) |
| Anti CD8 whole Mab | 8/8 (100%) |
| Anti CD4 whole Mab | 8/20 (40%) |
| Anti CD4 scFv | 16/23 (70%) |

Topical administration of scFv will be started on the day of disease induction and will be continued for 28 days. In both sets of experiments, some animals will be killed at specific time points after immunization with melanin, and the eyes taken for histology and immunohistochemistry to determine the composition of any cellular infiltrate and whether it has been altered by treatment. Should either test scFv significantly reduce the incidence of uveitis, then attempts will be made to reinduce disease by further immunization with melanin, to determine whether non-responsiveness has been induced. We will examine the effect of treatment on existing disease by administering scFv on the first day that cells and flare are observed in the anterior chamber, and daily thereafter for 5 days. Rats will be followed at the slit-lamp and some eyes collected for histology.

EXAMPLE 5

Modulation of Corneal Allograft Rejection by scFv

The efficacy of scFvs directed against CD4, CD54, IL-2R, CD28, CD80 and CD86 in the prevention of corneal graft rejection in WF to F344 allografts will be examined. For the co-stimulatory molecules CD80 and CD86, a scFv cocktail will be used. Controls will include rats receiving no treatment, treatment with a scFv of irrelevant specificity, with anti-CD8 scFv, and with whole antibody. A small number of isografts will be performed to check for toxicity or other side effects. Systemic administration will be tested using protocols known to be effective for whole antibodies. Rats will be injected ip on days −3, 0, 3, 5 and 7 with respect to transplantation. Estimation of the amount of engineered fragment required for an effect in vivo will be established in preliminary experiments, based on the amount of whole antibody needed for similar effect, together with titration of scFv activity. ScFvs will then be tested topically for their ability to prevent the onset of rejection (direct application to the graft daily from the day of graft for 28 days), and to treat ongoing rejection (direct application daily for 5 days from the first day that corneal blood vessels first cross the graft-host junction or from the day that signs of anterior segment inflammation are observed, which ever occurs first). Some animals will be killed at specific time points after graft, and the eyes taken for histology and immunohistochemistry to determine the composition of any cellular infiltrate.

Whole monoclonal antibody directed against rat CD4 when given systemically as described above at approximately 0.2 mg/mL can prolong corneal graft survival, as shown in Table 2 below and by Ayliffe et al (1992, Brit J Ophthalmol 76: 602–6), and He at al (1991, Invest Ophthalmol Vis Sci 32: 2723–8).

TABLE 2

| Antibody | Graft Survival (days) |
| --- | --- |
| Control | 13, 14, 17, 23 |
| W3/25 | 9, 12, 20, >100 |
| OX35 + OX38 | 29, 29, >100, >100 |

EXAMPLE 6

Diagnosis and Treatment of Herpetic Keratitis by Antibody Fragments

To investigate the potential of scfvs as therapeutic agents for stromal herpetic keratitis, both the necrotising and recurrent models of disease will be used. Mice will receive topically applied scfv (anti-CD4, CD8, CD11b/c, IL-2R or HSV gpD antigen) in eye-drops or scFv of irrelevant specificity, 1 drop four times daily. An additional control group will receive topical 0.5% ophthalmic prednisolone phosphate and 3% acyclovir ophthalmic ointment (Zovirax, Glaxo-Wellcome), 4 times daily. Animals with necrotising disease will be treated from day 14 to day 21 after inoculation; animals with recurrent disease from day 2 to day 4 post-reactivation. Systemic administration of scFv will also be investigated. Efficacy will be measured clinically at the slit lamp and by endpoint immunohistochemistry and histology to determine the composition of the leucocytic infiltrate. For diagnostic purposes, the scFv to HSV gpD will be coupled to fluorescein, a fluorochrome already used in topical ophthalmic preparations that can readily be visualised using the blue light-source at the slit-lamp. After administration of the fluorochrome-tagged scFv as an eye-drop to the infected cornea, we will attempt to detect the presence of viral antigen in the cornea in situ by direct examination and by slit-lamp photography with the blue filter. In the necrotising HSV keratitis model, the potential of scFv for rapid diagnosis will be investigated in the third week after inoculation. In the recurrent keratitis model, eye-drops will be given on the third day post-reactivation. The results of direct examination will be correlated with histopathology and viral culture.

EXAMPLE 7

Diagnosis and Treatment of Acantliamoeba Keratitis by Antibody Fragments

Fluorochrome-labelled scFvs and dimerised fragments directed to a 40 kDa protein known to be present on the surface of both trophozoites and cysts will be generated. The appropriate IgG hybridoma is available from the ATCC. Porton rats will receive scFv eye-drops on day 4, 7 or 10 after inoculation with *Acanthamoeba castellanii* Neff. At these stages, there will be most trophozoites, trophozoites and cysts, or mostly cysts in their corneas, respectively. On each day, eye-drops containing various concentrations of the conjugated scFv will be given and the eyes will be examined and photographed using the slit lamp. The animals will then be killed and their eyes processed for histology. This will allow us to correlate the slit lamp observations with pathology. To investigate the potential therapeutic use of fragments, infected rats will be treated with unconjugated dimeric fragment topically every hour through the day from day 6 to day 10 after inoculation. Other rats will receive a control fragment only, or a combination of propamidine and polyhexamethylene biguanide, the current treatments of choice for amoebic keratitis. Treatment efficacy will be assessed by clinical score, histopathology, and quantification of viable amoebae by limiting dilution from homogenised corneas.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appendant claims.

What is claimed is:

1. A method of treating an ocular disorder, comprising topically administering to an eye of a patient in need of such treatment an effective amount of a sub-immunoglobulin sized antigen-binding molecule that is immuno-interactive with a target antigen associated with the disorder.

2. The method of claim 1, wherein the sub-immunoglobulin sized antigen-binding molecule does not comprise the Fc portion of an immunoglobulin molecule.

3. The method of claim 1, wherein the sub-immunoglobulin sized antigen-binding molecule comprises a synthetic Fv fragment.

4. The method of claim 1, wherein the sub-immunoglobulin sized antigen-binding molecule comprises a synthetic stabilised Fv fragment.

5. The method of claim 4, wherein the synthetic stabilised Fv fragment is a single chain Fv fragment.

6. The method of claim 1, wherein the sub-immunoglobulin sized antigen-binding molecule is a minibody.

7. The method of claim 1, wherein the target antigen is selected from the group consisting of an MHC molecule, a co-stimulatory molecule, an adhesion molecule, a receptor-associated molecule, a cytokine receptor and a viral surface antigen.

8. The method of claim 7, wherein the co-stimulatory molecule is selected from the group consisting of CD80, CD86 and CD152.

9. The method of claim 7, wherein the adhesion molecule is selected from the group consisting of CD11, CD 18, CD54 and CD62L.

10. The method of claim 7, wherein the receptor-associated molecule is selected from the group consisting of CD3, CD4, CD8, CD28, CD40, CD40L and CTLA4.

11. The method of claim 7, wherein the cytokine receptor is selected from the group consisting of the interleukin 2 receptor, a subunit of the interleukin 2 receptor, and the interferon γ receptor.

12. The method of claim 7, wherein the viral surface antigen is a herpes virus surface antigen.

13. The method of claim 12, wherein the herpes virus surface antigen is gD2 or gB2.

14. The method of claim 1, wherein the sub-immunoglobulin sized antigen-binding molecule is modified to prolong its half-life.

15. The method of claim 14, wherein the sub-immunoglobulin sized antigen-binding molecule is chemically modified with polyethylene glycol.

16. The method of claim 1, which further comprises the step of modulating the surface of said eye to improve penetration of the sub-immunoglobulin antigen-binding molecule into a desired intraocular region.

17. The method of claim 16, wherein the corneal epithelium of said eye is modulated by a penetration enhancer.

18. The method of claim 16, wherein the corneal epithelium of said eye is modulated by a penetration enhancer selected from the group consisting of benzalkonium chloride, capric acid, DMSO, dihydrocytochalasin B, digitonin, detergents and any combination thereof.

19. The method of claim 1, which further comprises the step of subjecting at least a portion of said eye to iontophoresis such that the sub-immunoglobulin sized antigen-binding molecule penetrates into a desired intraocular region.

20. The method of claim 1, wherein the ocular disorder is selected from the group consisting of corneal graft rejection, uveitis, inflammatory eye diseases, infectious eye diseases, ocular tumours, neovascular proliferative diseases, neovascular maculopathies, rheumatoid corneal melting disorders and autoimmune disorders.

21. The method of claim 1, wherein the sub-immunoglobulin sized antigen-binding molecule is administered topically in the form of an eye drop.

22. The method of claim 1, wherein the sub-immunoglobulin sized antigen-binding molecule is administered topically in the form of a collagen shield.

23. A method of diagnosing an ocular condition, comprising:
topically administering to a portion of an eye with a sub-immunoglobulin sized antigen-binding molecule that is immuno-interactive with a target antigen indicative of the condition; and
detecting the presence of a complex comprising the antigen-binding molecule and the target antigen.

24. The method of claim 23, wherein the sub-immunoglobulin sized antigen-binding molecule does not comprise the Fc portion of an immunoglobulin molecule.

25. The method of claim 23, wherein the sub-immunoglobulin sized antigen-binding molecule comprises a synthetic Fv fragment.

26. The method of claim 23, wherein the sub-immunoglobulin sized antigen-binding molecule comprises a synthetic stabilised Fv fragment.

27. The method of claim 26, wherein the synthetic stabilised Fv fragment is a single chain Fv fragment.

28. The method of claim 23, wherein the sub-immunoglobulin sized antigen-binding molecule is a minibody.

29. The method of claim 23, wherein the sub-immunoglobulin sized antigen-binding molecule has a detectable label associated therewith.

30. The method of claim 29, wherein the label is a fluorochrome.

31. The method of claim 30, wherein the fluorochrome is fluorescein.

32. The method of claim 23, wherein the sub-immunoglobulin sized antigen-binding molecule is modified to prolong its half-life.

33. The method of claim 32, wherein the sub-immunoglobulin sized antigen-binding molecule is chemically modified with polyethylene glycol.

34. The method of claim 23, wherein the step of topically administering comprises delivering the sub-immunoglobulin sized antigen-binding molecule in the form of an eye drop.

35. The method of claim 23, wherein the step of topically administering comprises delivering the sub-immunoglobulin sized antigen-binding molecule in the form of a collagen shield.

36. The method of claim 23, further comprising the step of modulating the surface of the eye to improve penetration of the sub-immunoglobulin sized antigen-binding molecule.

37. The method of claim 36, wherein the corneal epithelium of said eye is modulated by a penetration enhancer.

38. The method of claim 36, wherein the corneal epithelium of said eye is modulated by a penetration enhancer selected from the group consisting of benzalkonium chloride, capric acid, DMSO, dihydrocytochalasin B, digitonin, detergents and any combination thereof.

39. The method of claim 23, further comprising the step of subjecting at least a portion of the eye to iontophoresis.

40. The method of claim 23, wherein the ocular disorder is selected from the group consisting of corneal graft rejection, uveitis, inflammatory eye diseases, infectious eye diseases, ocular tumours, neovascular proliferative diseases, neovascular maculopathies, rheumatoid corneal melting disorders and autoimmune disorders.

41. A pharmaceutical composition formulated for topical administration for treatment or diagnosis of an ocular disorder, comprising a sub-immunoglobulin sized antigen-binding molecule that is immuno-interactive with a target antigen associated with the disorder, and a carrier.

42. The composition of claim 41, wherein the sub-immunoglobulin sized antigen-binding molecule does not comprise the Fc portion of an immunoglobulin molecule.

43. The composition of claim 41, wherein the sub-immunoglobulin sized antigen-binding molecule comprises a synthetic Fv fragment.

44. The composition of claim 41, wherein the sub-immunoglobulin sized antigen-binding molecule comprises a synthetic stabilised Fv fragment.

45. The composition of claim 44, wherein the synthetic stabilised Fv fragment is a single chain Fv fragment.

46. The composition of claim 41, wherein the sub-immunoglobulin sized antigen-binding molecule is a minibody.

47. The composition of claim 41, wherein the target antigen is selected from the group consisting of an MHC molecule, a co-stimulatory molecule, an adhesion molecule, a receptor-associated molecule, a cytokine receptor and a viral surface antigen.

48. The composition of claim 47, wherein the co-stimulatory molecule is selected from the group consisting of CD80, CD86 and CD152.

49. The composition of claim 47, wherein the adhesion molecule is selected from the group consisting of CD11, CD18, CD54 and CD62L.

50. The composition of claim 47, wherein the receptor-associated molecule is selected from the group consisting of CD3, CD4, CD8, CD28, CD40, CD40L and CTLA4.

51. The composition of claim 47, wherein the cytokine receptor is selected from the group consisting of the interleukin 2 receptor, a subunit of the interleukin 2 receptor, and the interferon γ receptor.

52. The composition of claim 47, wherein the viral surface antigen is a herpes virus surface antigen.

53. The composition of claim 52, wherein the herpes virus surface antigen is gD2 or gB2.

54. The composition of claim 41, wherein the sub-immunoglobulin sized antigen-binding molecule is modified to prolong its half-life.

55. The composition of claim 54, wherein the sub-immunoglobulin sized antigen-binding molecule is chemically modified with polyethylene glycol.

56. The composition of claim 41, which further comprises a penetration enhancer.

57. The composition of claim 56, wherein the penetration enhancer is selected from the group consisting of benzalkonium chloride, capric acid, DMSO, dihydrocytochalasin B, digitonin, detergents and any combination thereof.

58. The composition of claim 41 in the form of an eye drop.

59. The composition of claim 41 in the form of a collagen shield.

60. An ocular composition formulated for topical administration to the eye comprising a sub-immunoglobulin sized antigen-binding molecule that is immuno-interactive with a target antigen in the eye.

61. The method of claim 40, wherein the infectious eye diseases are selected from the group consisting of: viral conjunctivitis, bacterial conjunctivitis, viral keratitis, bacterial keratitis and chlamydial keratitis.

62. The method of claim 40, wherein the autoimmune disorder is ocular penthigold.

63. The method of claim 20, wherein the infectious eye diseases are selected from the group consisting of: viral conjunctivitis, bacterial conjunctivitis, viral keratitis, bacterial keratitis and chlamydial keratitis.

64. The method of claim 20, wherein the autoimmune disorder is ocular penthigold.

* * * * *